US008653258B2

(12) United States Patent
Wang et al.

(10) Patent No.: US 8,653,258 B2
(45) Date of Patent: Feb. 18, 2014

(54) COMPOSITIONS FOR REGULATING OR MODULATING QUORUM SENSING IN BACTERIA, METHODS OF USING THE COMPOUNDS, AND METHODS OF REGULATING OR MODULATING QUORUM SENSING IN BACTERIA

(75) Inventors: Binghe Wang, Marietta, GA (US); Nanting Ni, Atlanta, GA (US); Junfeng Wang, Beijing (CN); Chung-Dar Lu, Roswell, GA (US); Han-Ting Chou, Atlanta, GA (US); Minyong Li, Shandong (CN); Shilong Zheng, Atlanta, GA (US); Yunfeng Cheng, Atlanta, GA (US); Hanjing Peng, Chamblee, GA (US)

(73) Assignee: Georgia State University Research Foundation, Inc., Atlanta, GA (US)

( * ) Notice: Subject to any disclaimer, the term of this patent is extended or adjusted under 35 U.S.C. 154(b) by 279 days.

(21) Appl. No.: 12/597,825

(22) PCT Filed: Jun. 6, 2008

(86) PCT No.: PCT/US2008/066028
§ 371 (c)(1),
(2), (4) Date: Oct. 27, 2009

(87) PCT Pub. No.: WO2009/029317
PCT Pub. Date: Mar. 5, 2009

(65) Prior Publication Data
US 2010/0137249 A1    Jun. 3, 2010

Related U.S. Application Data

(60) Provisional application No. 60/933,735, filed on Jun. 8, 2007.

(51) Int. Cl.
*C07F 5/02* (2006.01)
*C12Q 1/02* (2006.01)
(52) U.S. Cl.
USPC ............... 544/37; 544/229; 546/13; 548/110; 549/4; 549/213; 558/384; 560/60; 564/8; 568/6
(58) Field of Classification Search
None
See application file for complete search history.

(56) References Cited

U.S. PATENT DOCUMENTS 5,041,440 A * 8/1991 Kubota et al. ............... 514/231.5
5,308,860 A    5/1994 Shaber
5,668,161 A * 9/1997 Talley et al. ................. 514/365
2004/0180829 A1 9/2004 Bassler et al.

FOREIGN PATENT DOCUMENTS

| GB | 2063870 A | 6/1981 |
|---|---|---|
| WO | 99/10321 A2 | 3/1999 |
| WO | 0247681 A1 | 6/2002 |
| WO | 2003018029 A1 | 3/2003 |
| WO | 03077844 A2 | 9/2003 |
| WO | 2004004712 A1 | 1/2004 |
| WO | 2005005598 A2 | 1/2005 |
| WO | 2005021559 A2 | 3/2005 |
| WO | 2005100384 A2 | 10/2005 |

OTHER PUBLICATIONS

Janczewski et al., Influence of molecular structure on the optical properties of sulfinyl compounds. VI. Diphenylsulfinylacetic acids, Roczniki Chemii (1961), 35, 1155-7 (CAS Abstract).*
Van Leusen et al., Chemistry of alpha-diazosulfones. IV. Preparation of N-arylsulfonylmethyl)urethans and N-(alkylsulfonylmethyl)urethans, Recueil des Travaux Chimiques des Pays-Bas (1965), 84(2), 140-50 (CAS Abstract).*
Huppatz, J. L., Convenient synthesis of ethyl sulfonylacetates, Australian J. Chem. (1971), 24(3), 653-5 (CAS Abstract).*
Hepworth, H., and Stevenston, N. B., Action of the Grignard Reagent on Certain Organo-Sulfur Compounds, 119 J. Chem. Soc., Trans. 1188-98 (1921).*
Barnikow et al., Synthesis of CH-acidic Thionocarboxylic Acid Esters, 8(9) Fed. Rep. Ger. Zeitschrift Fuer Chemie 335 (1968).*
Pratanata et al., Mass Spectra of the Arylsulfonyl Derivatives of Methyl Acetates, 27(11) Australian J. Chem. 2361-4 (1974).*
European Search Report dated Oct. 31, 2012.
Britsun, et al., "Cycloacylation of Phenylsulfonyl-N-R-thioacetamides by Compounds Containing an Activated Multiple Bond," Chemistry of Heterocyclic Compounds, Kluwer Academic Publishers-Consultants Bureau, NE, vol. 41, No. 11, Nov. 1, 2005, pp. 1437-1438.
Zhong, et al.,"Design and Synthesis of Quinolin-2(1H)-one Derivatives as Potent CDK5 Inhibitors," Bioorganic & Medicinal Chemistry Letters, Pergamon, Elsevier Science, GB, vol. 17, No. 19, Aug. 6, 2007, pp. 5384-5389.
Zakrzewski, et al., "Investigations of Fungicidal Properties of Substituted Phenylsulphonylacetic Acid Esters and Amides," Chemical Abstracts Service, Columbus, OH, 2001.
Lee, et al., "Radical Alkylation of bis(silyloxy)enamine derivatives of organic nitro compounds," Angewandte Chemie, Sep. 18, 2006, vol. 45, No. 37, pp. 6182-6186.
Huppatz, "Convenient Synthesis of Ethyl Sulfonylacetates," Chemical Abstracts Service, Columbus, OH, 1971, Australian Journal of Chemistry (1971) 24(3) pp. 653-655.

(Continued)

*Primary Examiner* — Janet L Andres
*Assistant Examiner* — Timothy R. Rozof
(74) *Attorney, Agent, or Firm* — Thomas|Horstemeyer, LLP

(57) ABSTRACT

The present disclosure encompasses compounds and compositions that are useful as specific AI-2 antagonists for the control of bacterial quorum sensing. Although the AI-2 antagonists according to the present disclosure may not have bactericidal effect, their ability to attenuate virulence, drug resistance, and/or biofilm formation have therapeutic benefits. In addition, the AI-2 antagonists of the present disclosure can also be used as tools to probe bacterial AI-2 functions. The present disclosure also encompasses methods for inhibiting or attenuating microbial virulence, biofilm formation, and drug resistance. The methods are suitable for preventing bacteria from accruing and forming extensive biofilms that may be a health or hygiene hazard or a physical issue, such as in the blockage of water or fuel lines.

6 Claims, 17 Drawing Sheets

(56) References Cited

OTHER PUBLICATIONS

Barnikow, et al., "Synthesis of CH-acidic thionocarboxylic acid esters," Chemical Abstracts Service, Columbus, OH 1969 Zeitschrift Fuer Chemi (1968) 8(9), 335.

Zhou, et al., "Chemoselective Oxidation of Organic Sulfides to Sulfones with Sodium Perborate," Chemical Abstracts Service, Columbus, OH 1992 Wuji Huaxue Xuebao (1992), 8(1), pp. 88-90.

Persson, et al., "Rational Design and Synthesis of new quorum-sensing inhibitors derived from acylated homoserine lactones and natural products from garlic," Organic & Biomolecular Chemistry, Jan. 21, 2005, vol. 3, No. 2, pp. 253-262.

Li, et al., "Structure-based discovery and experimental verification of novel AI-2 quorum sensing inhibitors against *Vibrio harveyi*," Chemmedchem, vol. 3, No. 8, Aug. 2008, pp. 1242-1249.

\* cited by examiner 10  11  12  13  14

COMPOSITIONS FOR REGULATING OR MODULATING QUORUM SENSING IN BACTERIA, METHODS OF USING THE COMPOUNDS, AND METHODS OF REGULATING OR MODULATING QUORUM SENSING IN BACTERIA

CROSS-REFERENCE TO RELATED APPLICATION

This application claims priority to the PCT application entitled "COMPOSITIONS FOR REGULATING OR MODULATING QUORUM SENSING IN BACTERIA, METHODS OF USING THE COMPOUNDS, AND METHODS OF REGULATING OR MODULATING QUORUM SENSING IN BACTERIA," having serial number PCT/US2008/066028, filed on Jun. 6, 2008. This application also claims priority to and benefit of U.S. Provisional Patent Application No. 60/933,735, filed on Jun. 8, 2007, which is incorporated by reference in its entirety.

FIELD OF THE DISCLOSURE

The present disclosure relates to compounds, compositions and methods of use thereof for regulating quorum sensing in bacteria.

BACKGROUND

Health problems resulting from bacterial infections, once declining in importance, are experiencing a resurgence for several reasons: (1) the wide-spread emergence of drug-resistant bacterial strains, (2) the continuing problem of bacterial biofilm formation, which results in drug resistance and causes a variety of persistent infections including chronic middle ear, bone, and heart valve infections; infections related to implanted medical devices; and lung infections in people with cystic fibrosis and other chronic problems, and (3) terrorists and rouge states may use bacteria as biological weapons. The biofilm issue is gaining importance because of medical advances that allow an increasing percentage of individuals to have an improved quality of life by relying on implanted medical devices, artificial heart valves, replacement joints, and the like. In addition, the general population is living longer, and there is an increasing number of people with chronic health problems, such as asthma, diabetes, and compromised immune functions that may give rise to persistent infections. Once persistent infections are established, biofilm formation may become a problem, which in turn leads to drug resistance problems.

In addition to human health issues, biofilm formation is also a problem in industry (e.g., water, sanitation, and fuel industries) and animal care including aquatic animal care. In most cases, a non-sterile environment with nutrients usable by one or more microbial species is conducive to the colonization of a surface by the microbe(s), whereupon they will proliferate and secrete polysaccharide and other compounds that together form a film that protects the underlying organisms, and can prove troubling to remove. The complex and dense nature of the secreted matrix of a biofilm typically affords resistance to penetration by antimicrobials such as antibiotics and disinfectants. For all the reasons stated above, there is an ever expanding need for the development of new strategies to deal with bacterial infection issues that have no current effective solution.

SUMMARY

The present disclosure encompasses compounds and compositions including such compounds that are useful as specific AI-2 antagonists for the control of bacterial quorum sensing. Although the AI-2 antagonists according to the present disclosure may not have bactericidal effect, their ability to attenuate virulence, drug resistance, and/or biofilm formation can be beneficial therapeutically. In addition, the AI-2 antagonists of the present disclosure can also be used as tools to probe bacterial AI-2 functions.

The present disclosure further encompasses methods for inhibiting or attenuating, bacterial virulence, biofilm formation, and drug resistance. An embodiment of the method is suitable for preventing bacteria from accruing and forming extensive biofilms that may be a health or hygiene hazard or a physical issue, such as in the blockage of water or fuel lines. Compositions of the present disclosure can be used to treat hard, rigid structures or surfaces such as drain pipes, glazed ceramic, porcelain, glass, metal, wood, chrome, plastic, vinyl, and formica, or soft flexible structures or surfaces such as shower curtains, upholstery, laundry, and carpeting. In addition, methods of the present disclosure can be used to treat woven and non-woven and/or porous and non-porous surfaces.

One aspect of the present disclosure therefore provides compounds, wherein the compound is an antagonist of a microbial quorum sensing activity, and wherein the antagonist is selected from the formulas shown in FIGS. 3, 7, 8, 13A, 13B, 14, 18, and 19. In various embodiments of the compounds of the disclosure, the compound comprises a boronic acid moiety and is selected from the formulas as shown in FIGS. 13 and 14 of the disclosure.

In other embodiments of the disclosure, the compound may be further selected from 5-IQBA, 4-IQBA, and DDCQ of the disclosure.

In various embodiments of the compounds of the disclosure, the compound may be selected from the formulas as shown in FIGS. 18 and 19 of the disclosure.

The methods of the disclosure may include administering or contacting an effective amount of an AI-2 antagonist to a structure or surface of a structure that is intended to be bacteria-free. For example, the surface of a medical device to be implanted into an animal or a human subject may be provided with a coating comprising at least one of the AI-2 antagonists of the present disclosure, thereby hindering or preventing altogether the formation of a biofilm that may prove injurious or even fatal to the recipient subject.

It is contemplated that the compositions of the present disclosure are useful for the coating of an effective amount of the compounds to food preparation surfaces, such as kitchen counters, cutting boards, sinks, stoves, refrigerator surfaces, or on sponges and other cleaning implements, such as mops and wipes, or to bathroom surfaces, such as toilets, sinks, bathtubs, showers, and drains. Other suitable treatable surfaces are floors and window surfaces The compositions of the disclosure may also be suitable for application to clothing and other woven and soft surfaces. This may be performed by methods using a wipe, sponging or soaking method or by a laundering or detergent method.

In an embodiment, the method includes administering or contacting an effective amount of the compounds to, especially surfaces that are exposed to moisture, such as kitchen floor, shower stalls, and food production areas.

The compositions of the disclosure may also be added directly to drinking or bathing water for delivery to the surface where a biofilm has formed, or has the potential to form, such as in the interior of a pipe, food production machinery (e.g., raw meat, fish, pork, and poultry processing equipment, as well as fruit and vegetable processing equipment), sanitation equipment, processing areas, and conduits that carry raw materials or finished products.

The compositions of the disclosure may be delivered to a subject in need thereof by providing a mouthwash or a toothpaste for the treatment of dental caries, acne treatment, cleaning and disinfecting contact lenses, and medically implanted devices that are permanent such as an artificial heart valve or hip joint, and those that are not permanent such as indwelling catheters, pacemakers, surgical pins, and the like.

The antimicrobial advantages of the compositions of the disclosure may further include a topical application to an animal or a human subject having a surface lesion such as a burn or laceration to prevent the colonization or infection of the wound.

BRIEF DESCRIPTION OF THE DRAWINGS

FIG. 6A is the control having a doubling time: 78.9 min. FIG. 6B is with compound 10 at 67.8 μM and a doubling time of 72.1 mins. FIG. 6C is with compound 11 at 115.6 μM and a doubling time of 74.3 min.

FIG. 11A is a control having a doubling time of 79.4 min. FIG. 11B is with compound 5-IQBA at 125 μM, doubling time 99.2 min. FIG. 11C is with compound 4-IQBA at 125 μM, doubling time 80.4 min. FIG. 11D is with DDCQ at 250 μM, doubling time 78.7 min.

DETAILED DESCRIPTION OF THE DISCLOSURE

Figure 1:
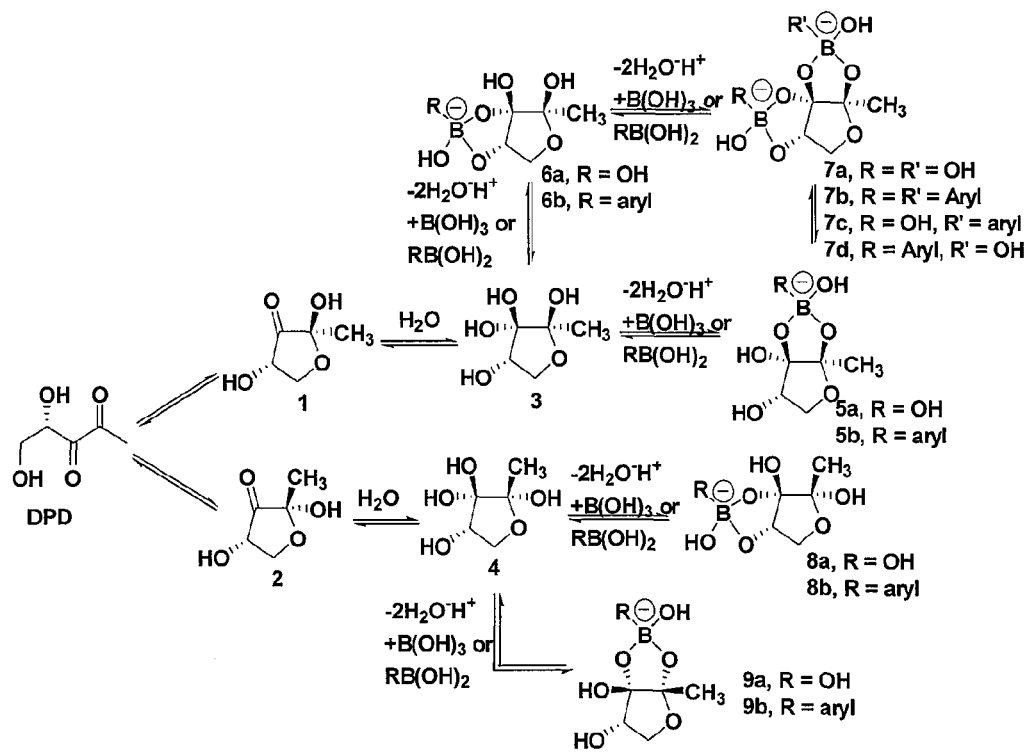
FIG. 1 schematically illustrates that DPD may exist in different forms and complexes with borate and boronic acids.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified. In addition, the phrase "about 'x' to 'y'" includes "about 'x' to about 'y'".

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

DEFINITIONS

Generally the terms and phrases used herein have their art-recognized meaning which can be found by reference to standard texts, journal references and contexts known to those skilled in the art. The following definitions are provided to clarify their specific use in the context of this disclosure.

The terms "treating" or "treatment" of bacteria as used herein refer to preventing a condition from occurring in a structure, system, or host that may be predisposed to the bacteria but does not yet experience or exhibit symptoms of bacteria (prophylaxis) and/or inhibiting bacterial growth (slowing or arresting its development). The treatment may be bactericidal or bacteriastatic.

The term "modulate(s)" as used herein includes inhibition, attenuation, control, diminishment, prevention, induction, detachment, removal, cleaning, and/or dispersal bacterial formation of growth, development, or behavior. The term "modulate" further refers to generating any change in the colonization or proliferation of a microbial population, to the induction of any change resulting in the increase or decrease of a physiological activity of a microbial population The term "inhibition" of bacteria means either hindering its proliferation, or making it incapable of accomplishing some functions that it usually accomplishes (e.g., preventing, stopping, or slowing the growth of bacteria, bacterial virulence, drug resistance, biofilm formation, and the like.)

The terms "microbe, microbial, and microbial population" as used herein refer to any type microorganism including, but not limited to, bacteria, viruses, fungi, algae, protozoa and the like. In particular, a "microbial population" as referred to in the present disclosure is a population of bacteria. It is contemplated that a microbial population that may respond to contact with the compositions of the disclosure may be a homogeneous population that is of one bacterial species only, or a heterogeneous and mixed population of at least two bacterial species (and may be in combination with other microorganisms). The bacterial species that comprise the microbial population may be Gram-positive or Gram-negative, and the populations may be all Gram-positive species or Gram-negative species, or a combination thereof.

The terms "bacteria" or "bacterial" as used herein include, but are not limited to, Gram positive and Gram negative bacteria. The term "bacteria" can include, but are not limited to, species of the genera *Abiotrophia, Achromobacter, Acidaminococcus, Acidovorax, Acinetobacter, Actinobacillus, Actinobaculum, Actinomadura, Actinomyces, Aerococcus, Aeromonas, Afipia, Agrobacterium, Alcaligenes, Alloiococcus, Alteromonas, Amycolata, Amycolatopsis, Anaerobospirillum, Anaerorhabdus, Arachnia, Arcanobacterium, Arcobacter, Arthrobacter, Atopobium, Aureobacterium, Bacteroides, Balneatrix, Bartonella, Bergeyella, Bifidobacterium, Bilophila Branhamella, Borrelia, Bordetella, Brachyspira, Brevibacillus, Brevibacterium, Brevundimonas, Brucella, Burkholderia, Buttiauxella, Butyrivibrio, Calymmatobacterium, Campylobacter, Capnocytophaga, Cardiobacterium, Catonella, Cedecea, Cellulomonas, Centipeda, Chlamydia, Chlamydophila, Chromobacterium, Chyseobacterium, Chryseomonas, Citrobacter, Clostridium, Collinsella, Comamonas, Corynebacterium, Coxiella,*

*Cryptobacterium, Delftia, Dermabacter, Dermatophilus, Desulfomonas, Desulfovibrio, Dialister, Dichelobacter, Dolosicoccus, Dolosigranulum, Edwardsiella, Eggerthella, Ehrlichia, Eikenella, Empedobacter, Enterobacter, Enterococcus, Erwinia, Erysipelothrix, Escherichia, Eubacterium, Ewingella, Exiguobacterium, Facklamia, Filifactor, Flavimonas, Flavobacterium, Francisella, Fusobacteriumi, Gardnerella, Gemella, Globicatella, Gordona, Haemophilus, Hafnia, Helicobacter, Helococcus, Holdemania Ignavigranum, Johnsonella, Kingella, Klebsiella, Kocuria, Koserella, Kurthia, Kytococcus, Lactobacillus, Lactococcus, Lautropia, Leclercia, Legionella, Leminorella, Leptospira, Leptotrichia, Leuconostoc, Listeria, Listonella, Megasphaera, Methylobacterium, Microbacterium, Micrococcus, Mitsuokella, Mobiluncus, Moellerella, Moraxella, Morganella, Mycobacterium, Mycoplasma, Myroides, Neisseria, Nocardia, Nocardiopsis, Ochrobactrum, Oeskovia, Oligella, Orientia, Paenibacillus, Pantoea, Parachlamydia, Pasteurella, Pediococcus, Peptococcus, Peptostreptococcus, Photobacterium, Photorhabdus, Plesiomonas, Porphyrimonas, Prevotella, Propionibacterium, Proteus, Providencia, Pseudomonas, Pseudonocardia, Pseudoramibacter, Psychrobacter, Rahnella, Ralstonia, Rhodococcus, Rickettsia Rochalimaea Roseomonas, Rothia, Ruminococcus, Salmonella, Selenomonas, Serpulina, Serratia, Shewenella, Shigella, Simkania, Slackia, Sphingobacterium, Sphingomonas, Spirillum, Staphylococcus, Stenotrophomonas, Stomatococcus, Streptobacillus, Streptococcus, Streptomyces, Succinivibrio, Sutterella, Suttonella, Tatumella, Tissierella, Trabulsiella, Treponema, Tropheryma, Tsakamurella, Turicella, Ureaplasma, Vagococcus, Veillonella, Vibrio, Weeksella, Wolinella, Xanthomonas, Xenorhabdus, Yersinia,* and *Yokenella.* Examples of bacterial species include, but are not limited to, *Mycobacterium tuberculosis, M. bovis, M. typhimurium, M. bovis* strain BCG, BCG substrains, *M. avium, M. intracellulare, M. africanum, M. kansasii, M. marinum, M. ulcerans, M. avium* subspecies *paratuberculosis, Staphylococcus aureus, Staphylococcus epidermidis, Staphylococcus equi, Streptococcus pyogenes, Streptococcus agalactiae, Listeria monocytogenes, Listeria ivanovii, Bacillus anthracis, B. subtilis, Nocardia asteroides, Streptococcus viridans* group, *Actinomyces israelii, Propionibacterium acnes, Clostridium tetani, Clostridium botulinum, Pseudomonas aeruginosa, Vibrio cholera, Actinobacillus pleuropneumoniae, Pasteurella haemolytica, Pasteurella multocida, Legionella pneumophila, Salmonella typhi, Brucella abortus, Chlamydi trachomatis, Chlamydia psittaci, Coxiella bumetti, Escherichia coli, Neiserria meningitidis, Neiserria gonorrhea, Haemophilus influenzae, Haemophilus ducreyi, Yersinia pestis, Yersinia enterolitica, Escherichia coli, E. hirae, Brucella abortus, Burkholderia cepacia, Burkholderia pseudomallei, Francisella tularensis, Bacteroides fragilis, Fudobascterium nucleatum,* and *Cowdria ruminantium,* or any strain or variant thereof.

The term "biofilm" as used herein refers to biological films that develop and persist at interfaces in aqueous environments, especially along the inner walls of conduit material in industrial facilities, in household plumbing systems, on medical implants, or as foci of chronic infections. Biofilms may also form on biological surfaces such as teeth, or any other surfaces natural or artificial that may be exposed to or in contact with non-sterile aqueous environments that may include nutrients suitable for the colonization and proliferation of the microorganisms. These biological films are composed of microorganisms embedded in an organic gelatinous matrices composed of one or more matrix polymers that are secreted by the resident microorganisms. Biofilms can develop into macroscopic structures several millimeters or centimeters in thickness and can cover large surface areas. These biological formations can play, for example, a role in restricting or entirely blocking flow in plumbing systems or fuel lines and often decrease the lifespan or longevity of materials through corrosive action mediated by the embedded bacteria. Biofilms are also capable of trapping nutrients and particulates that can contribute to their enhanced development and stability. Biofilms can also prevent penetration of antimicrobial agents, which may lead to persistent infections.

The term "contacting" as used herein refers to exposure by close physical contact of the composition to a structure, system, or host, or bacteria.

The term "effective amount" as used herein refers to an amount of the subject compound at least sufficient to achieve a desired modulation of the activity or physiological property of a microbial population. The effective amount is determined, at least in part, upon the compound used, the microbial species present, the structure, system, or host, and the desired level of regulation. Modulating the activity or physiological property of the microbial population includes, but is not limited to, slowing, attenuating, inhibiting, or enhancing the colonization of a surface or proliferation of bacteria, inhibiting the formation of a biofilm, and the like. Modulation includes slowing the formation of bacteria or new bacteria if some bacteria are already present, inhibiting the formation of a biofilm.

The term "antagonist of the AI-2 quorum sensing pathway" as used herein refers to compounds that may compete with AI-2 inducers such as DPD. Such antagonists are also able to inhibit the induction of physiological responses of bacteria by activators of the AI-2 quorum sensing apparatus.

As used herein, the term "active agents" refers to compositions of the present disclosure that elicit responses (e.g., inhibit the AI-2 quorum sensing pathway) at the site of application (contact) to a structure, system, or host.

To the extent that the disclosed compounds may exist in the form of a salt, the disclosed compounds can form salts that are also within the scope of this disclosure. Reference to each compound herein is understood to include reference to salts and their deuterated forms thereof, unless otherwise indicated. The term "salt(s)," as employed herein, denotes acidic and/or basic salts formed with inorganic and/or organic acids and bases. In addition, when a compound contains both a basic moiety and an acidic moiety, zwitterions ("inner salts") may be formed and are included within the term "salt(s)" as used herein. For delivery to an animal or a human subject, pharmaceutically acceptable (i.e., non-toxic, physiologically acceptable) salts are preferred, although other salts are also useful (e.g., in isolation or purification steps which may be employed during preparation). Salts of the compounds may be formed, for example, by the compound reacting with an amount of acid or base, such as an equivalent amount, in a medium such as one in which the salt precipitates or in an aqueous medium followed by lyophilization.

The disclosed compounds that contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates (such as tosylates), undecanoates, and the like.

The disclosed compounds that contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dihydroabietyl)ethylenediamine), N-methyl-D-glucamines, N-methyl-D-glucamides, t-butyl amines, and salts with amino acids such as arginine, lysine, and the like.

Solvates of the compounds are also contemplated herein. Solvates of the compounds are preferably hydrates.

To the extent that the disclosed compounds, and salts thereof, may exist in their tautomeric form, all such tautomeric forms are contemplated herein as part of the present disclosure. All stereoisomers of the present compounds, such as those which may exist due to asymmetric carbons on the various substituents, including enantiomeric forms (which may exist even in the absence of asymmetric carbons) and diastereomeric forms, are contemplated within the scope of this disclosure. Individual stereoisomers of the compounds of the disclosure may, for example, be substantially free of other isomers, or may be admixed, for example, as racemates or with all other, or other selected, stereoisomers. The chiral centers of the compounds of the present disclosure can have the S or R configuration as defined by the IUPAC 1974 Recommendations.

The term "composition" as used herein generally refers to any mixture, powder, solution, suspension, gel, ointment or the like which contains the active compounds of the present disclosure and/or a carrier, and any additional optional inactive ingredients and is in a form suitable for delivery to a host, structure, or system. Thus, the term "composition" includes various dosage forms of compositions of the present disclosure.

The terms "virtual" or "virtual screening" as used herein refer to screening by computer-based analysis databases as described in Example 1 below.

The term "organism" or "host" refers to any living entity comprised of at least one cell. A living organism can be as simple as, for example, a single eukaryotic cell or as complex as a mammal, including a human being. As used herein, the term "host" includes humans, mammals (e.g., cats, dogs, horses, chicken, pigs, hogs, cows, fish, crabs, shrimps, cattle, and other), and other living species that are in need of treatment. In particular, the term "host" includes humans.

Discussion

The present disclosure, as embodied and broadly described herein, encompasses AI-2 antagonists, compositions, methods of modulating (e.g., inhibiting) quorum sensing, methods of regulating (e.g., inhibiting or controlling) bacterial growth, and the like. The disclosure further encompasses methods of regulating microbial, and in particular bacterial, virulence, biofilm formation, and drug resistance by exposing the structure, system, or host to a composition comprising one or more of the compounds described herein. Embodiments of the present disclosure can be used to modulate one or more types of bacteria (e.g., a plurality of types of bacteria can be present or could form on the structure, system, or host), and in particular those species of bacteria that express AI-2 induced quorum sensing.

The present disclosure, therefore, provides compositions that may comprise one or more of the compounds shown in FIGS. 3, 7, 8, 13A, 13B, 14, 18 and 19. Additional details regarding the compounds and the AI-2 quorum pathway are described in the examples and the corresponding figures. The compounds are AI-2 antagonists and modulate (e.g., inhibit) the AI-2 quorum sensing pathway. AI-2 mediated quorum sensing is especially important because it is functional in both Gram-positive and Gram-negative bacteria. Thus, the compounds and methods of the present disclosure can regulate one or more properties of these targeted Gram-positive and Gram-negative bacteria, if the property is operably linked to the AI-2 quorum sensing apparatus. Although the compounds of the present disclosure appear not to have a bactericidal effect, the compounds have the ability to regulate virulence, drug resistance and biofilm formation, which can be of great clinical significance because these problems tend to be hard to resolve with currently available antibiotics. One or more compounds can be used in the compositions of the present disclosure. In addition, compositions of the present disclosure can be used in conjunction with antibacterial compositions.

Quorum Sensing

Quorum sensing is a mechanism whereby microorganisms, and in particular bacteria, communicate with each other and exhibit community-wide behavior coordination through the secretion and detection of chemical signals called autoinducers (AIs). Quorum sensing has been demonstrated in a large number of bacteria species/strains and important in regulating bacterial virulence, drug resistance, expression of efflux transporters, and biofilm formation, and therefore is attracting attention in the antimicrobial field.

Several major types of quorum sensing compounds have been identified. For example, in Gram-negative bacteria, N-acylhomoserine lactones (AHLs) are quorum sensing molecules. In Gram-positive bacteria there are many autoinducing peptides (AIPs) that mediate quorum sensing processes. Other quorum sensing molecules are known, including epinephrine/norepinephrine.

Among all the known autoinducers, autoinducer 2 (AI-2 of Scheme 1, FIG. 1) is the only one that mediates quorum sensing in both Gram-positive and Gram-negative bacteria, and therefore is sometimes referred to as the "universal quorum sensing autoinducer."

The AI-2 Quorum Sensing Pathway and its Relevance to Pathogenicity.

Though the specific function of AI-2 mediated quorum sensing may vary among different bacterial species, it is widely accepted that AI-2 is a signal molecule in quorum sensing and plays important roles in regulating virulence, biofilm formation, and associated drug resistance. For example, AI-2 has been found to regulate biofilm formation by a wide variety of bacteria including *Escherichia coli, Salmonella typhimurium, Bacillus subtilis, Streptococcus oralis Actinomyces naesiundii, Eikenella corrodens, Streptococcus anginosus, Bacillus cereus, Vibrio cholera*, etc. AI-2 also induces, for example, the expression of multi-drug resistant genes such as AcrAB in *E. coli*; regulate virulence genes in the pathogenic strain *E. coli* O157 H7; cause significant expression level changes for at least 242 genes of the *E. coli* genome; and regulate production of proteins needed for infection by Lyme disease spirochetes. Inhibition of the AI-2 quorum sensing pathway could allow for the effective intervention of pathologically relevant events mediated by AI-2.

AI-2 and its Chemistry.

In bacteria, AI-2 is synthesized from S-adenosylmethionine in three steps. The last step is catalyzed by the enzyme LuxS to produce (S)-4,5-dihydroxy-2,3-pentanedione (DPD of Scheme 1, FIG. 1), and homocysteine. DPD can exist in different forms, and readily undergoes cyclization to yield two stereoisomers (1, 2, Scheme 1, FIG. 1), which can undergo further hydration to give forms 3 and 4. In aqueous solution, all five species (DPD, and 1-4) exist in equilibrium. Synthetic DPD shows essentially the same biological activities as AI-2 produced by bacteria.

One unique property of DPD is its ability to form boric acid complexes (5-9) when in its hydrated forms 3 and 4. The formation of the borate complexes as shown in Scheme 1, FIG. 1, is not surprising in its chemistry since boric and boronic acids have been known to bind strongly and reversibly to compounds with vicinal diols. This is especially true if the diols have cis geometry and are part of a five-membered ring. Despite the strong binding between boric/boronic acid(s) with diols, the discovery that one of DPD's biologically active forms is the borate complex (5a) is significant and unique in the quorum sensing field. Indeed, there are very few examples where boric acid complexing is required for a natural product's biological activity.

Protein Targets Binding to AI-2.

A least two bacterial protein targets may bind to AI-2. The first one is LuxP, which exists in *V. harveyi* and *V. cholera* (the LuxP proteins from these two species share 62% homology). LuxP binds AI-2 in its boric acid complexed form (5a). A second protein target is LsrB and other members of the Lsr ("LuxS regulated") family of transporter proteins responsible for the uptake of DPD (and thus essential for DPD-mediated quorum sensing). LsrB has been found in *S. typhimurium* and *E. coli* and its crystal structure has also been defined. LsrB binds DPD in a different form (4) that does not contain boron.

Antimicrobial Agents Targeting Bacterial Quorum Sensing.

Many furanones are known to inhibit the AI-1 (AHL) quorum sensing pathway due to their structural similarity with the β-lactone moiety of AHLs. There is also an example of an halogenated furanone showing non-specific inhibition of AI-2 quorum sensing. In this case, (5Z)-4-bromo-5-(bromomethylene)-3-butyl-2(5H)-furanone may inhibit many AI-2-mediated gene expressions at about 323 µM concentration, though the mechanism of this inhibition is not understood. There is no indication that it is through binding to the LuxP protein. It should also be noted that (5Z)-4-bromo-5-(bromomethylene)-3-butyl-2(5H)-furanone is also a strong Michael acceptor and thus a good alkylator. Therefore, it is unclear whether non-specific alkylation may be a contributing factor for the AI-2 inhibition by this compound. In addition, one compound having specific inhibition of two different target proteins: LuxR (for AI-1 or AHLs) and LuxP (for AI-2) is unusual. The high concentration (323 µM) of the halogenated furanone used may also suggest general toxicity. Studies have shown that similar furanones and halogenated furanones, including some that are AI-1 (AHL) inhibitors, are known to have general cytotoxicities, possibly due to alkylation and/or alkylation followed by halide elimination.

Quorum sensing inhibitors/antagonists alone may not be expected to have bactericidal effect, especially since their biological role is in cell-cell communication. However, their ability to attenuate virulence, drug resistance and biofilm formation may be of clinical significance because these are problems that are difficult to resolve with currently available antibiotics. Targeting quorum sensing as a way of limiting a bacterial infection has been demonstrated by experiments using inhibitors of the AI-1 (AHL) pathway in Gram-negative bacteria, and the AIP pathway in Gram-positive bacteria. For example, mice treated with synthetic antagonists of *Staphylococcus aureus* AIP showed resistance to infection; furanones, which also are inhibitors of AHL-mediated quorum sensing, may attenuate bacterial virulence in mice and increase the sensitivity toward antibiotics of *Pseudomonas aeruginosa* in a biofilm. Quorum sensing inhibitors encompassed by the present disclosure may be useful, for example, in preventing Staphylococcal biofilm-associated infections and biofilm formation and toxin production in animal models. Quorum sensing inhibitors may inhibit *B. anthracis* growth and virulence-gene expression, suppress drug-resistant Staphylococcal infection in rat model, reduce the mortalities caused by Vibriosis in rainbow trout, increase survival rate in mice and reduce biofilm formation in vivo by drug resistant *Staphylococcus epidermidis*.

Available in vitro and in vivo data show that inhibiting quorum sensing in general is a promising approach to control bacterial infection by attenuating virulence, biofilm formation, and drug resistance. However, no specific antagonists of the AI-2 quorum sensing pathway have been reported. Since this is the pathway that functions in both Gram-positive and Gram-negative species, such AI-2 antagonists as encompassed by the present disclosure may be useful have the potential to be "broad-spectrum" antimicrobial agents.

Specific Targeting of the AI-2 Pathway by Quorum Sensing Antagonists.

Despite the extensive effort in studying the biological problems of the AI-2 universal quorum sensing pathway, the medicinal chemistry has had limited success in devising useful inhibitors of the pathway. Many analogs have less potent agonist effects than the natural ligand, AI-2. A trifluoromethyl analog of DPD has been prepared that shows agonistic activities.

Cinnamaldehyde inhibits both AI-1 and AI-2 quorum sensing pathways through unknown non-specific actions. Given that cinnamaldehyde is a Michael acceptor, a non-specific protein alkylation may contribute to its mechanism of action, which would lead to non-specific antimicrobial effect, and consequently affect quorum sensing. For example, cinnamaldehyde and analogs can covalently modify cysteines in protein (cinnamaldehyde $EC_{50}$: 19 µM). AI-2 antagonists reported that may specifically target the key receptor/transporter proteins of LuxP and LsrB are not known.

The present disclosure, therefore, encompasses compounds and compositions including such compounds that are especially useful as specific AI-2 antagonists for the control of bacterial quorum sensing. Although the AI-2 antagonists according to the present disclosure may not have any bactericidal effect, their ability to attenuate virulence, drug resistance and biofilm formation can be beneficial therapeutically. In addition, the AI-2 antagonists of the present disclosure can also be used as tools to probe bacterial AI-2 functions.

Embodiments of the present disclosure further methods for inhibiting or attenuating, for example, virulence, biofilm formation, and drug resistance. The methods are suitable for preventing bacteria from accruing and forming extensive biofilms that may be a health or hygiene hazard or a physical issue, such as in the blockage of water or fuel lines. Compositions of the present disclosure are particularly useful in treating hard, rigid structures or surfaces such as drain pipes, glazed ceramic, porcelain, glass, metal, wood, chrome, plastic, vinyl, and formica, or soft flexible structures or surfaces such as shower curtains, upholstery, laundry, and carpeting. In addition, methods of the present disclosure can be used to treat both woven and non-woven and porous and non-porous surfaces would be suitable.

The methods of the disclosure may include administering or contacting an effective amount of an AI-2 antagonist to a structure or surface of a structure that is intended to be bacteria-free. For example, the surface of a medical device to be implanted into an animal or a human subject may be provided with a coating comprising at least one of the AI-2 antagonists of the present disclosure, thereby hindering or preventing altogether the formation of a biofilm that may prove injurious or even fatal to the recipient subject.

It is contemplated that the compositions of the present disclosure are useful for the coating of an effective amount of the compounds to food preparation surfaces, such as kitchen counters, cutting boards, sinks, stoves, refrigerator surfaces, or on sponges and other cleaning implements, such as mops and wipes, or to bathroom surfaces, such as toilets, sinks, bathtubs, showers, and drains. Other suitable treatable surfaces are floors and window surfaces The compositions of the disclosure may also be suitable for application to clothing and other woven and soft surfaces. This may be performed by methods using a wipe, sponging or soaking method or by a laundering or detergent method.

In an embodiment, the method includes administering or contacting an effective amount of the compounds to, especially surfaces that are exposed to moisture, such as kitchen floor, shower stalls, and food production areas.

The compositions of the disclosure may also be added directly to drinking or bathing water for delivery to the surface where a biofilm has formed, or has the potential to form, such as in the interior of a pipe, food production machinery (e.g., raw meat, fish, pork, and poultry processing equipment, as well as fruit and vegetable processing equipment), sanitation equipment, processing areas, and conduits that carry raw materials or finished products.

The compositions of the disclosure may be delivered to a subject in need thereof by providing a mouthwash or a toothpaste for the treatment of dental caries, acne treatment, cleaning and disinfecting contact lenses, and medically implanted devices that are permanent such as an artificial heart valve or hip joint, and those that are not permanent such as indwelling catheters, pacemakers, surgical pins, and the like.

The antimicrobial advantages of the compositions of the disclosure may further include a topical application to an animal or a human subject having a surface lesion such as a burn or laceration to prevent the colonization or infection of the wound.

The emergence of drug-resistant bacteria and fungi presents a significant medical and public health. Consequently, there is an urgent need for the development of antimicrobial agents that can overcome the drug resistance problems. Bacteria and fungi generally develop drug resistance in four ways: producing metabolizing enzymes for the degradation of the drugs, modifying their targets to render the drugs ineffective, expressing a high level of efflux proteins that "pump" the drug out in order to lower its concentration, and inducing biofilm formation to prevent permeation of drugs into the bacteria.

In this regard, methods of the present disclosure can use (e.g., administer to the host and/or apply to the devices) the composition to inhibit bacteria formation or inhibit growth in medically implanted devices that are permanent devices (e.g., an artificial heart valve or hip joint), and those that are not permanent devices (e.g., indwelling catheters, pacemakers, surgical pins, and the like) to regulate bacteria as it relates to the medically implanted devices.

The compositions of the present disclosure can be in the form of a mixture, a powder, a solution, a suspension, a gel, an ointment, a suppository, in a slow-release matrix, immobilized form on a surface, a granule, a lotion, a liniment, an aerosol, a patch, a tincture, and the like or the like which contains the active compounds of the present disclosure. Each of the embodiments disclosed herein can be introduced to the structure, system, or host via methods such as, but not limited to, disposing directly onto the structure, disposing in a fluid that interacts with the structure or system, via injection, via a drop, via an aerosol, and the like. The composition can be disposed on or incorporated into structures or systems such as, but not limited to, fabrics, solid surfaces such as those described above, medical devices, machinery, as well as other structures described herein. The compositions of the present disclosure may optionally also include other components (e.g., active and non-active). The other components can include, but are not limited to, excipients, solubilizers, stabilizers, surfactants, toxicity agents, viscosity modifying agents, buffers, preservatives, and the like.

Where such forms exist, the compounds of the present disclosure may include analogues, homologues, isomers, or derivatives thereof that have similar desired results (e.g., regulation of bacteria). The compositions of the present disclosure include an acceptable salt of the compound and/or a acceptable polymorph, solvate, hydrate, dehydrate, co-crystal, anhydrous, or amorphous form thereof that have similar desired results (e.g., regulation of bacteria).

The compositions of the present disclosure can be liquids or lyophilized or otherwise dried formulations and include diluents of various buffer content (e.g., Tris-HCl, acetate, phosphate), pH and ionic strength, additives such as albumin or gelatin to prevent absorption to surfaces, a surfactant such as a polysorbate surfactant (e.g., TWEEN 20, TWEEN 40, TWEEN 60, and TWEEN 80), a phenoxypolyethoxyethanol surfactant (e.g., TRITON X-100, X-301, X-165, X-102, and X-200, and TYLOXAPOL) Pluronic F68, or sodium dodecyl sulfate, solubilizing agents (e.g., glycerol, polyethylene glycerol), antioxidants (e.g., ascorbic acid, sodium metabisulfite), preservatives (e.g., Thimerosal, benzyl alcohol, and parabens), bulking substances or tonicity modifiers (e.g., lactose, and mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts. Such compositions can influence the physical state, solubility, stability, rate of in vivo release, and rate of in vivo clearance, controlled or sustained release compositions include formulation in lipophilic depots (e.g., fatty acids, waxes, and oils). Since it is known that certain anti-fungal agents that may be included in the compositions of the present disclosure, such as itraconazole, are sparingly soluble in water, the solubility of such compounds may be increased by complexation with cyclodextrins or derivatives thereof as described in U.S. Pat. No. 4,764,604. In exemplary embodiments of the present disclosure itraconazole is solubilized by manual homogenization with carboxy methyl cellulose.

For topical applications, the pharmaceutically acceptable carrier may take the form of a liquid, cream, foam, lotion, or gel, and may additionally comprise organic solvents, emulsifiers, gelling agents, moisturizers, stabilizers, surfactants, wetting agents, preservatives, time release agents, and minor amounts of humectants, sequestering agents, dyes, perfumes, and other components commonly employed in pharmaceutical compositions for topical administration.

Further, as used herein "pharmaceutically acceptable carriers" are well known to those skilled in the art and include, but are not limited to, 0.01-0.1M and preferably 0.05M phosphate buffer or 0.8% saline. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Preservatives and other additives may also be present, such as, for example, antimicrobials, antioxidants, collating agents, inert gases and the like.

Controlled or sustained release compositions include formulation in lipophilic depots (e.g., fatty acids, waxes, oils). Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds. Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

Examples of suitable oily vehicles or solvents for use with the present disclosure are vegetable or animal oils such as sunflower oil or fish-liver oil. For formulation in liquid form for application in drop or spray form the compositions or their physiologically tolerated derivatives such as salts, esters, N-oxides, and the like are converted into a solution, suspension, or emulsion, if desired with the substances customary and suitable for this purpose, for example, solubilizers or other auxiliaries. Examples are: sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycol are preferred liquid carriers.

In addition, if desired, the composition can contain minor amounts of auxiliary substances such as wetting or emulsifying agents, or pH buffering agents that enhance the effectiveness of the active ingredient. Generally the pH of formulations of the present disclosure varies from about 4.0 to about 8.0; preferably the pH of the formulation is about 6.0.

An active component can be formulated into the composition as neutralized pharmaceutically acceptable salt forms. Pharmaceutically acceptable salts include the acid addition salts that are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For topical administration to body surfaces using, for example, creams, gels, drops, patches, and the like, the active compounds or their physiologically tolerated derivatives such as salts, esters, N-oxides, and the like are prepared and applied as solutions, suspensions, or emulsions in a physiologically acceptable diluent with or without a pharmaceutical carrier.

Suitable salts of the compositions disclosed herein include pharmaceutically acceptable salts. Other salts may, however, be useful in the preparation of the compounds according to the present disclosure or of their pharmaceutically acceptable salts. Suitable pharmaceutically acceptable salts of the compounds of this disclosure include acid addition salts which may, for example, be formed by mixing a solution of the compound according to this disclosure with a solution of a pharmaceutically acceptable acid such as hydrochloric acid, sulphuric acid, methanesulphonic acids fumaric acid, maleic acid, succinic acid, acetic acid, benzoic: acid, oxalic acid, citric acid, tartaric acid, carbonic acid or phosphoric acid.

The compositions also include a carrier, for example a pharmaceutically acceptable carrier. Often the physiologically acceptable carrier is an aqueous pH buffered solution. Examples of physiologically acceptable carriers include buffers such as phosphate, borate, citrate and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™. The carrier is also suitable for intranasal delivery and can include water or a mild or dilute saline solution, preferably a physiologically balanced saline solution. Additionally, the ion concentration of the carrier can be adjusted to provide a mild antibacterial effect. Saline solutions are also commonly used as moisturizers at present. In an exemplary embodiment of the composition of the present disclosure, the carrier is carboxy methyl cellulose. The amounts of carrier utilized generally are in the range of from about 5% to about 75%, more preferably from about 5% to about 50%, most preferably from about 20% to about 30%.

One aspect of the present disclosure provides compounds, wherein the compound is an antagonist of a microbial quorum sensing activity, and wherein the antagonist is selected from the group consisting of the formulas shown in FIGS. 3, 7, 8, 13A, 13B, 14, 18, and 19.

Figure 13A:
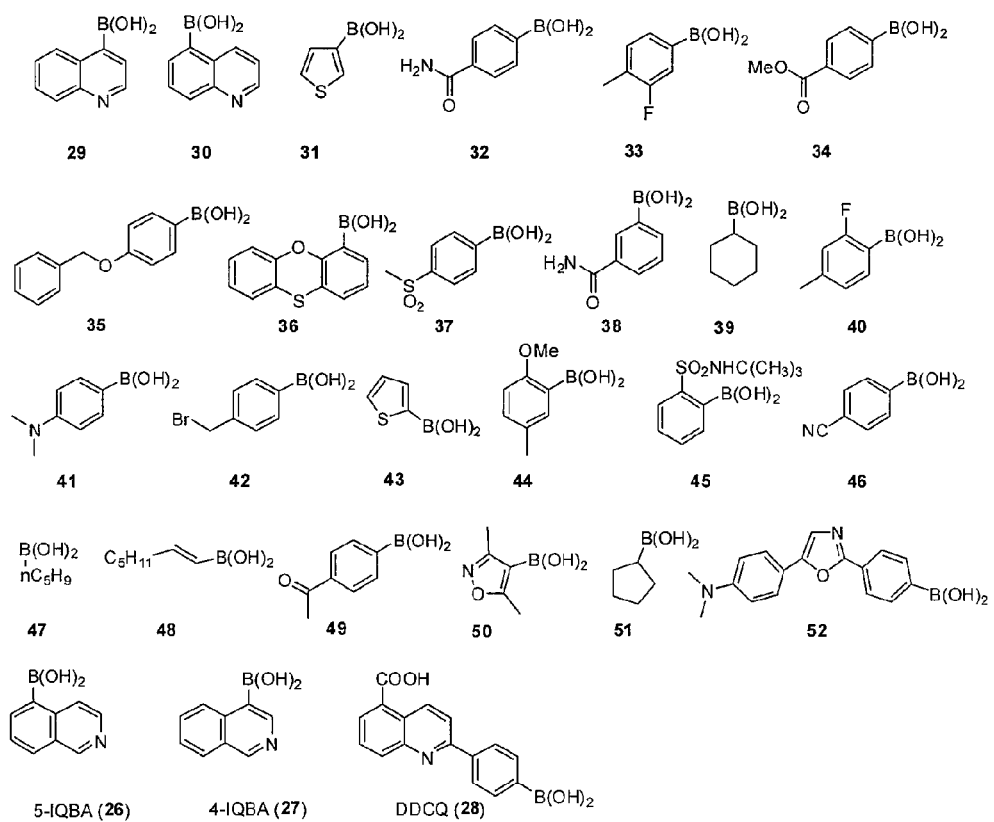
FIGS. 13A and 13B illustrate structures of boronic acids having inhibitory effects.
Figure 13B:
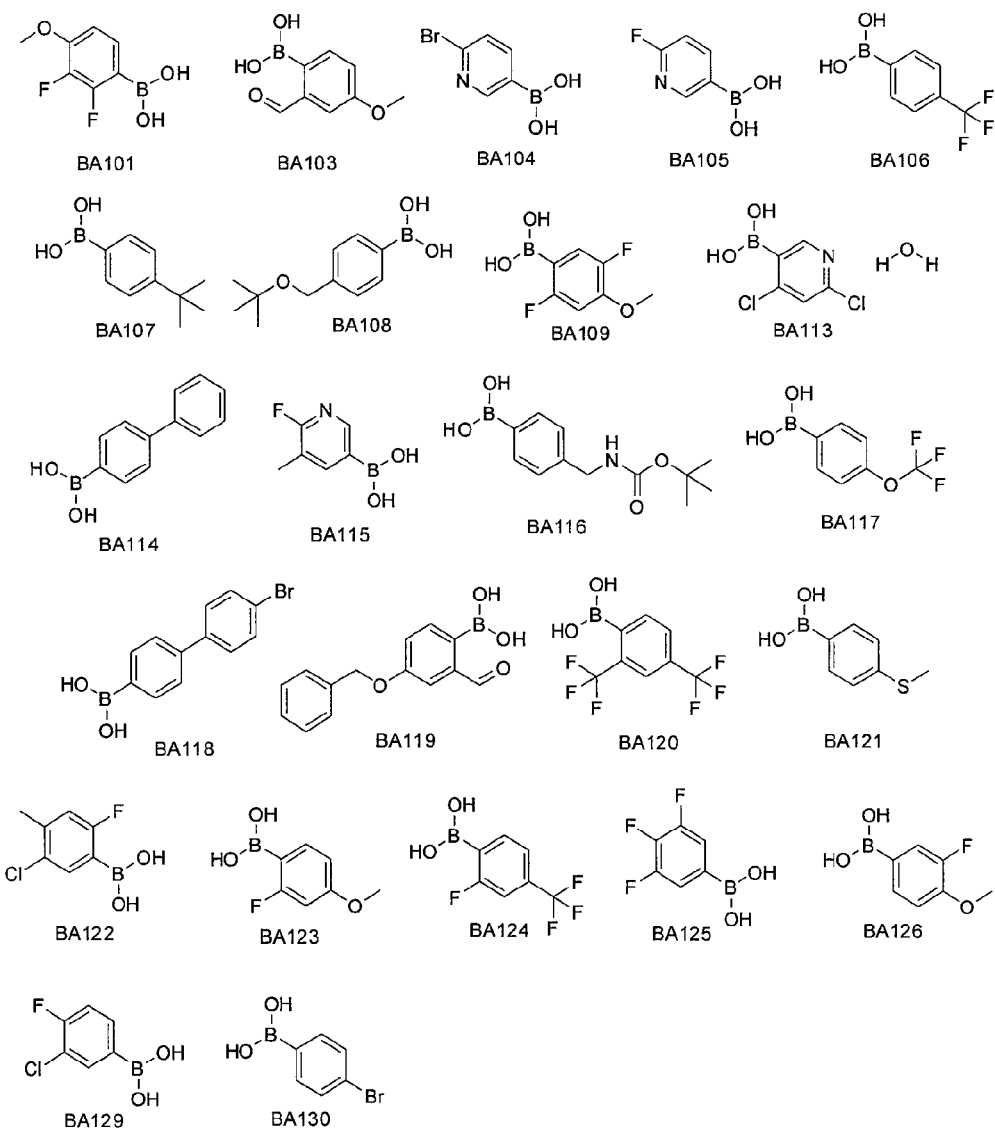
Figure 14:
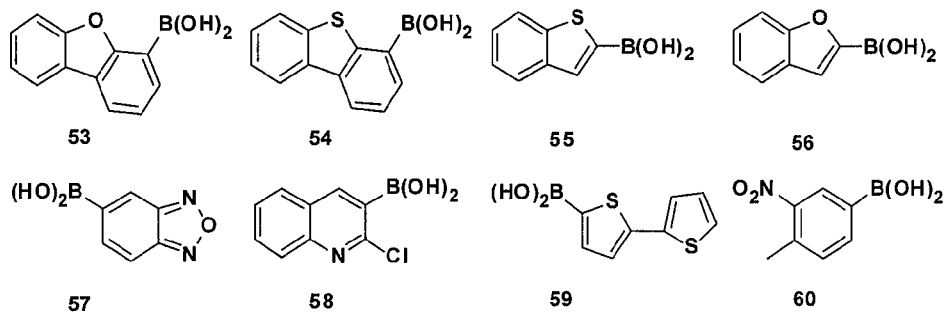
FIG. 14 illustrates the structures of boronic acids which have inhibitory effects and cytotoxicity.

In various embodiments of the compounds of the disclosure, the compound comprises a boronic acid moiety and is selected from the group consisting of the formulas as shown in FIGS. 13A, 13B, and 14.

In other embodiments of the disclosure, the compound may be further selected from the group consisting of 5-IQBA, 4-IQBA, and DDCQ.

Figure 18:
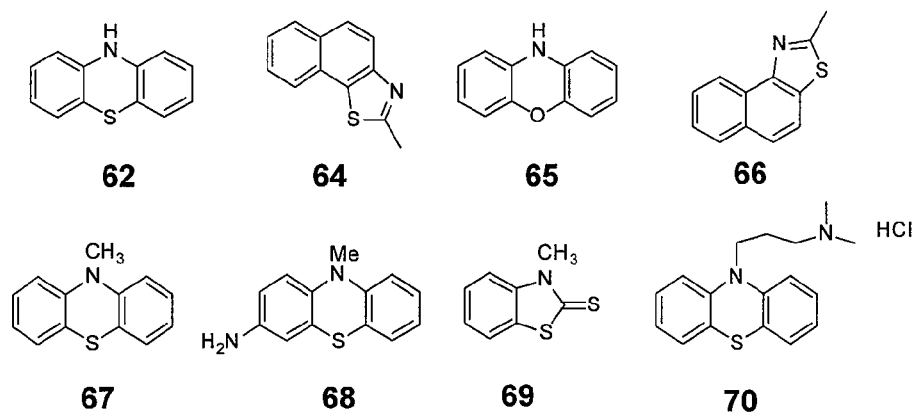
FIG. 18 illustrates the structures of phenothiazine (62) and its analogues having inhibitory effects.
Figure 19:
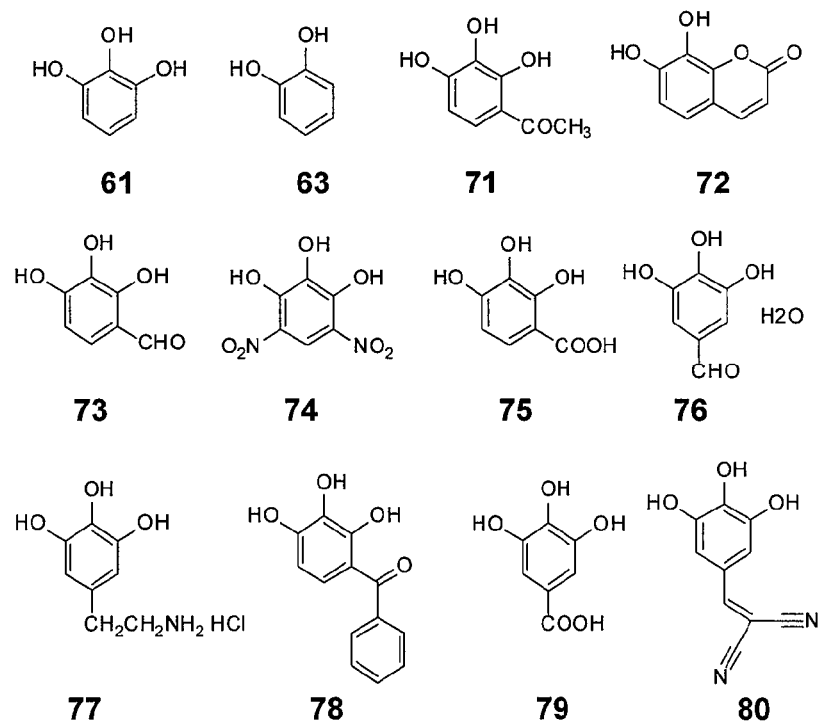
FIG. 19 illustrates the structures of pyrogallol (61) and its analogues having inhibitory effects.

In various embodiments of the compounds of the disclosure, the compound may be selected from the group consisting of the formulas as shown in FIGS. 18 and 19.

In this aspect of the disclosure, the microbial population is a bacterial population, and wherein the bacterial population is selected from the group consisting of: a population comprising at least one Gram-positive bacterial species, a population comprising at least one Gram-negative bacterial species, a mixed bacterial population comprising at least two Gram-positive bacterial species, a mixed bacterial population comprising at least two Gram-negative bacterial species, and a mixed bacterial population comprising at least one Gram-positive bacterial species and at least one Gram-negative bacterial species.

In this aspect of the disclosure, the compound may inhibit the luminescence produced by the bacterial species *Vibrio harveyi* in contact with (S)-4,5-dihydroxy-2,3-pentanedione and borate (DPD-borate).

Another aspect of the present disclosure is compositions for modulating quorum sensing in a microbial population, comprising at least one compound selected from the group consisting of the formulas shown in FIGS. 3, 7, 8, 13A, 13B, 14, 18, and 19, wherein the compound is in an amount effective for modulating quorum sensing of a microbial population.

In embodiments of this aspect of the disclosure, the compound may comprise a boronic acid moiety and may be selected from the group consisting of the formulas as shown in FIGS. 13A, 13B, and 14.

In embodiments of the compositions of the disclosure, the compound may be further selected from the group consisting of 5-IQBA, 4-IQBA, and DDCQ.

In embodiments of this aspect of the disclosure, the compound may be selected from the group consisting of the formulas as shown in FIGS. 18 and 19.

In embodiments of the disclosure the compositions are effective against a bacterial population.

In various embodiments, the bacterial population may be selected from the group consisting of: a population comprising at least one Gram-positive bacterial species, a population comprising at least one Gram-negative bacterial species, a mixed bacterial population comprising at least two Gram-positive bacterial species, a mixed bacterial population comprising at least two Gram-negative bacterial species, and a mixed bacterial population comprising at least one Gram-positive bacterial species and at least one Gram-negative bacterial species.

In one embodiment of the compositions of the disclosure, the compositions may further comprise a carrier.

In one embodiment of the compositions of the disclosure, the carrier is a pharmaceutically acceptable carrier.

Yet another aspect of the present disclosure provides methods for modulating a physiological activity of a microbial population, comprising: contacting a microbial population with an effective amount of a composition, wherein the composition comprises at least one compound selected from the group consisting of the formulas as shown in FIGS. 3, 7, 8, 13A, 13B, 18, and 19, and wherein the effective amount of the compound modulates at least one physiological activity of the bacterial population.

In various embodiments of the methods of this aspect of the disclosure, the compound may comprise a boronic acid moiety and is selected from the group consisting of the formulas as shown in FIGS. 13A, 13B, and 14.

In other embodiments of the compositions of the disclosure, the compound may be further selected from the group consisting of 5-IQBA, 4-IQBA, and DDCQ.

In still other embodiments of this aspect of the disclosure, the compound may be selected from the group consisting of the formulas as shown in FIGS. 18 and 19.

In embodiments of this method of the disclosure, the compositions may further comprise a carrier.

In one embodiment of this method, the carrier is a pharmaceutically acceptable carrier.

In various embodiments of the method of this aspect of the disclosure, the bacterial population may be selected from the group consisting of: a population comprising at least one Gram-positive bacterial species, a population comprising at least one Gram-negative bacterial species, a mixed bacterial population comprising at least two Gram-positive bacterial species, a mixed bacterial population comprising at least two Gram-negative bacterial species, and a mixed bacterial population comprising at least one Gram-positive bacterial species and at least one Gram-negative bacterial species.

In embodiments of this aspect of the disclosure, the modulated physiological activity of the bacterial population may be selected from the group consisting of bacterial cell growth, siderophore expression, bacterial virulence, biofilm formation, exopolysaccharide production, drug resistance, bacterial colony morphology, or a combination thereof.

Yet another aspect of the present disclosure are methods modulating biofilm formation on a surface, comprising: contacting a surface with an effective amount of a composition, wherein the composition comprises at least one compound selected from the group consisting of the formulas as shown in FIGS. 3, 7, 8, 13A, 13B, 18, and 19, and wherein the effective amount of the compound modulates biofilm formation on a surface.

In various embodiments of the methods of this aspect of the disclosure, the compound may comprise a boronic acid moiety and is selected from the group consisting of the formulas as shown in FIGS. 13A, 13B, and 14.

In other embodiments of the compositions of the disclosure, the compound may be further selected from the group consisting of 5-IQBA, 4-IQBA, and DDCQ.

In still other embodiments of this aspect of the disclosure, the compound may be selected from the group consisting of the formulas as shown in FIGS. 18 and 19.

In embodiments of this method of the disclosure, the amount of compound in the composition is effective in reducing the amount of a biofilm produced by the microbial population on the surface.

In other embodiments of the method, the amount of compound in the composition is effective in preventing the formation of a biofilm produced by the microbial population on the surface.

In various embodiments of the methods of this aspect of the disclosure, the microbial population is a bacterial population.

In various embodiments of the methods of this aspect of the disclosure, the bacterial population may be selected from the group consisting of: a population comprising at least one Gram-positive bacterial species, a population comprising at least one Gram-negative bacterial species, a mixed bacterial population comprising at least two Gram-positive bacterial species, a mixed bacterial population comprising at least two Gram-negative bacterial species, and a mixed bacterial population comprising at least one Gram-positive bacterial species and at least one Gram-negative bacterial species.

In one embodiment of the disclosure, the composition may further comprise a carrier.

In another embodiment, the carrier may be a pharmaceutically acceptable carrier.

In embodiments of the disclosure, the surface may be a surface of a medical device.

In other embodiments, the surface is a surface of a water or sewage pipe.

Yet another aspect of the present disclosure is a method for identifying an antagonist of the AI-2 bacterial quorum sensing system, comprising: combining in a first test chamber a test compound, DPD and a borate ions, combining in a second test chamber DPD and a borate ions, adding to the combinations in each of the first and second test chambers a population of cells of bacterial strain *Vibrio harveyi* MM32, determining the level of luminescence from each of the first and the second test chambers, and comparing the luminescence levels from the first and second test chambers, whereby if the level of luminescence of the first chamber is less than the luminescence level of the second chamber, the test compound is an antagonist of the AI-2 quorum sensing system of the bacteria.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

EXAMPLES

The disclosure, now having been generally described, will be more readily understood by reference to the following examples. This is done for the purpose of illustrating certain aspects and embodiments of the current discovery and is not intended to limit the disclosure.

Example 1

The Identification of AI-2 Antagonists Through Virtual Screening and Experimental (Bio-) Evaluation.

A model system comprising *Vibrio harveyi*, which is a Gram-negative marine microorganism and emits luminescence in response to AI-2 stimulation was used. This is also the most commonly used model system in studying AI-2 induced quorum sensing and the crystal structure of LuxP, the AI-2 receptor in *V. harveyi*, has been solved at 1.5 Angstrom resolution. It needs to be noted that *V. cholera* LuxP has a 62% homology identity with that of *V. harveyi*. Therefore, the results obtained may also have implications in *V. cholera* as well as other pathogens such as pathogenic *E. coli*. In the AI-2 quorum sensing pathway in *V. harveyi*, binding of DPD-boric acid complex (5a, Scheme 1 as shown in FIG. 1) to the LuxP protein initiates a cascade of events related to quorum sensing. In addition, it also leads to luminescence production, which makes it easy to monitor AI-2-initiated quorum sensing.

Figure 2:
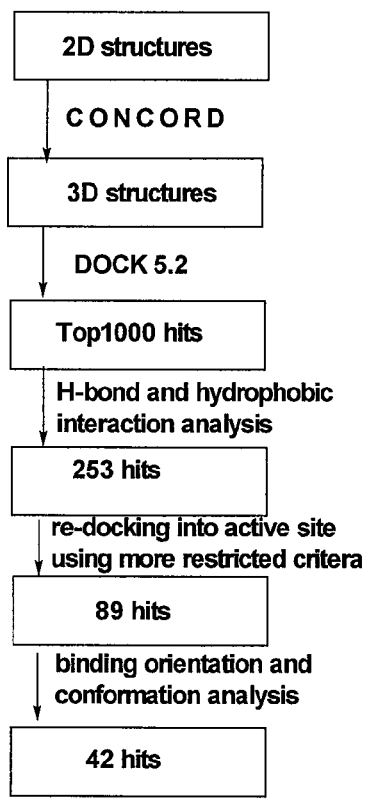
FIG. 2 illustrates the "virtual" screening steps in search of LuxP "binders."
Figure 3:
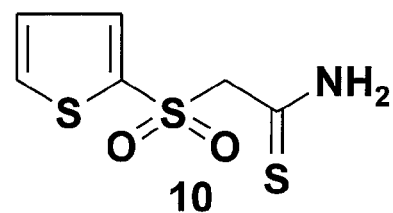
FIG. 3 illustrates two compounds identified by the "virtual" and bio-screening methods of the disclosure.
Figure 3:
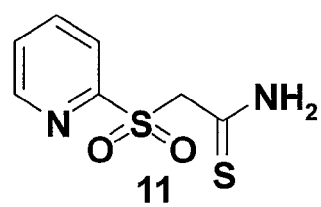

To identify small molecule compounds that can bind to LuxP with high affinity and specificity and therefore possibly function as AI-2 antagonists, a search for lead compounds through virtual screening was performed. The general scheme of this screening process is shown in FIG. 2.

Fourteen commercial databases including Chembridge, ASINEX, Maybridge, Specs, and which have a total of about 1.7 million compounds, were searched. The 2-D structures of compounds in these databases were first converted into 3-D structures and assigned partial charges for each compound (Gastiger-Hückel). Then the DOCK v5.2 molecular docking program was used to do the initial virtual screening with these compounds.

Re-analysis of the virtual screening results was conducted using drug-like properties, consensus scoring evaluation (ChemScore, PLP, ScreenScore, ChemGauss and Shape-Gauss), absorption, distribution, metabolism, excretion and toxicity (ADMET) prediction, as well as hydrogen bond and hydrophobic profiles and binding orientation examination. As a final step, manual intervention using detailed binding orientation and conformational analysis resulted in 42 candidate molecules suitable for a follow-on biological evaluation, as shown in FIGS. 3, 7, 8, and 13A-15A.

Example 2

Biological Screening.

The candidate compounds identified as described in Example 1, above, were tested for their ability to inhibit AI-2 induced quorum sensing using the MM32 strain of *V. harveyi*. The MM32 strain is known to have only the AI-2 pathway, and not the AI-1 pathway, but does not produce AI-2 itself. The *V. harveyi* bacteria can also emit luminescence upon AI-2 induced quorum sensing stimulation. Therefore, the ability of the "virtually" identified compounds to inhibit luminescence production in the presence of DPD and boric acid was examined.

MM32 bacteria were streak-seeded on fresh LM plates and cultured in the presence of kanamycin (50 µg/mL) and chloramphenicol (10 µg/mL). Colonies appeared after overnight incubation at 30° C. A single colony was picked up from the LM plate. This strain was grown for 16 hrs with aeration at 175 r.p.m and at 30° C. in 2 mL of Autoinducer Bioassay (AB) medium with antibiotics (kanamycin 50 µg/mL and chloramphenicol 10 µg/mL). The culture was then diluted to an $OD_{600}$ 0.7. This preinoculum was grown in AB-Fe medium with 1.2 mM of iron to $OD_{600}$ 1.0-1.1. The resulting inoculum culture was then diluted 5000-fold in fresh AB medium.

Figure 4:
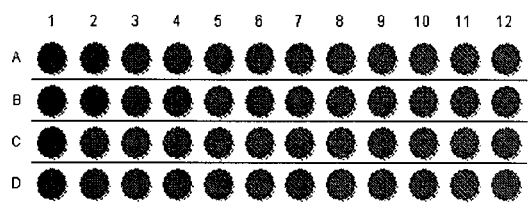
FIG. 4 illustrates the results of luminescence intensity studies. Rows A and B: compound 10; rows C and D: compound 11. Concentrations were from high to low and from left to right, with 2-fold serial dilutions staring with 452 μM for rows A and B, and 462 μM for rows C and D.

Solutions of the test compounds in AB medium were prepared in 96-well plates. To these solutions, freshly synthesized DPD (pH=7) solution was added for a final concentration of 5 µM. Boric acid was added to give a final concentration of 1 mM. After the addition of bacteria in AB medium, the micro plates were covered with a non-toxic plate sealer and incubated at 30° C. with aeration for 3-4 hrs. Light production was measured every half hour using a Perkin-Elmer luminescence microplate reader, as shown in FIG. 4, for example.

In an initial round of screening, the concentration of the test compounds was fixed at 100 µg/mL (about 200-600 µM). Those that showed more than 60% inhibition at this concentration were re-evaluated for their concentration dependent inhibition of luminescence emission by *V. harveyi*.

Figure 5A:
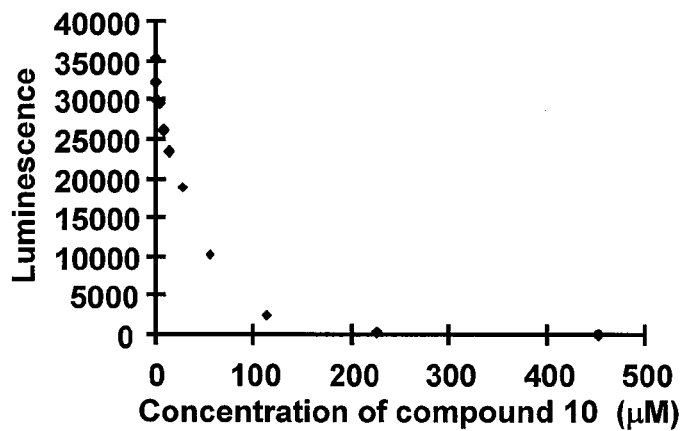
FIGS. 5A and 5B illustrate graphs showing the concentration-dependent inhibition of $V.\ harveyi$ luminescence by compound 10 (FIG. 5A, $IC_{50}$: 34.5±2.5 μM) and 11 (FIG. 5B, $IC_{50}$: 55.0±7.0 μM). Concentrations of compounds are from high to low, with 2-fold serial dilutions staring with 451.8 μM for compound 10 and 462.4 μM for compound 11.
Figure 5B:
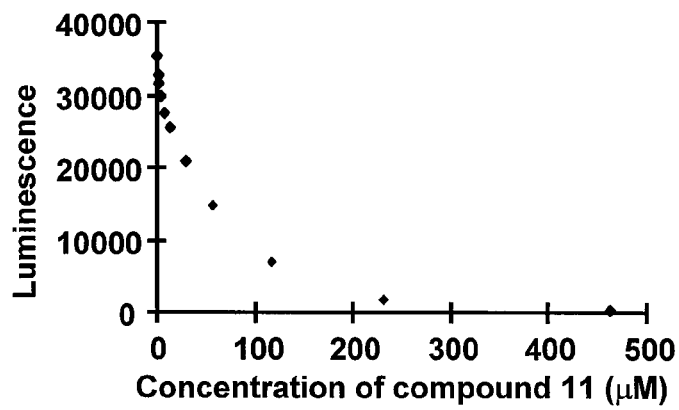

Among the compounds generated from our "virtual" database screening, several showed inhibitory activity. For example, FIG. 4 shows the microplate reader results with the compounds 10 and 11 illustrated in FIG. 3 with the luminescence intensity represented by the intensity of color with red being the most intense. FIGS. 5A and 5B show the concentration-dependent luminescence intensity decrease of *V. harveyi* in the presence of the test compounds 10 and 11. The $IC_{50}$ values of the two compounds were determined as approximately 35 and 55 µM, respectively.

Figure 6A:
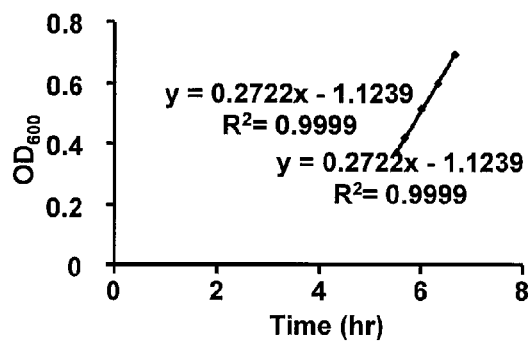
FIGS. 6A-6C illustrate graphs showing bacterial growth curves.
Figure 6B:
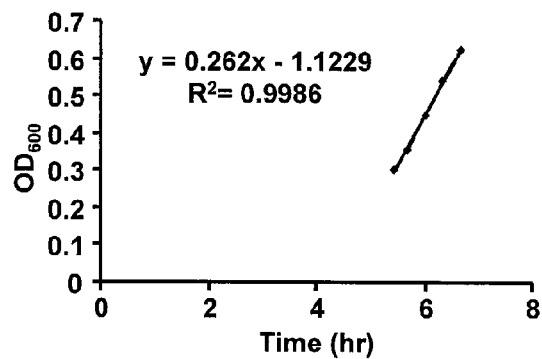
Figure 6C:
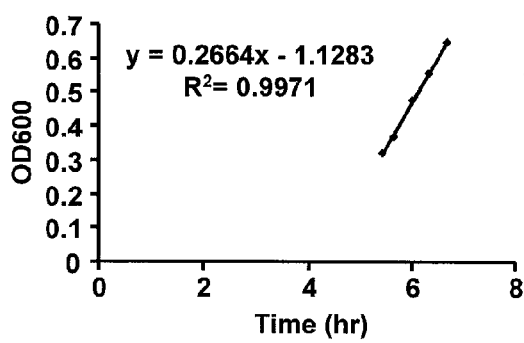
Figure 7:
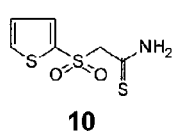
FIG. 7 illustrates the structures of effective compounds selected by virtual screening.
Figure 7:
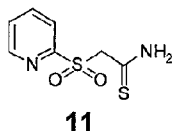
Figure 7:
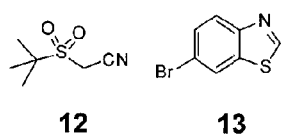
Figure 7:
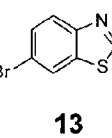
Figure 7:
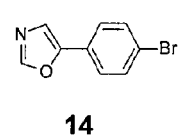
Figure 8:
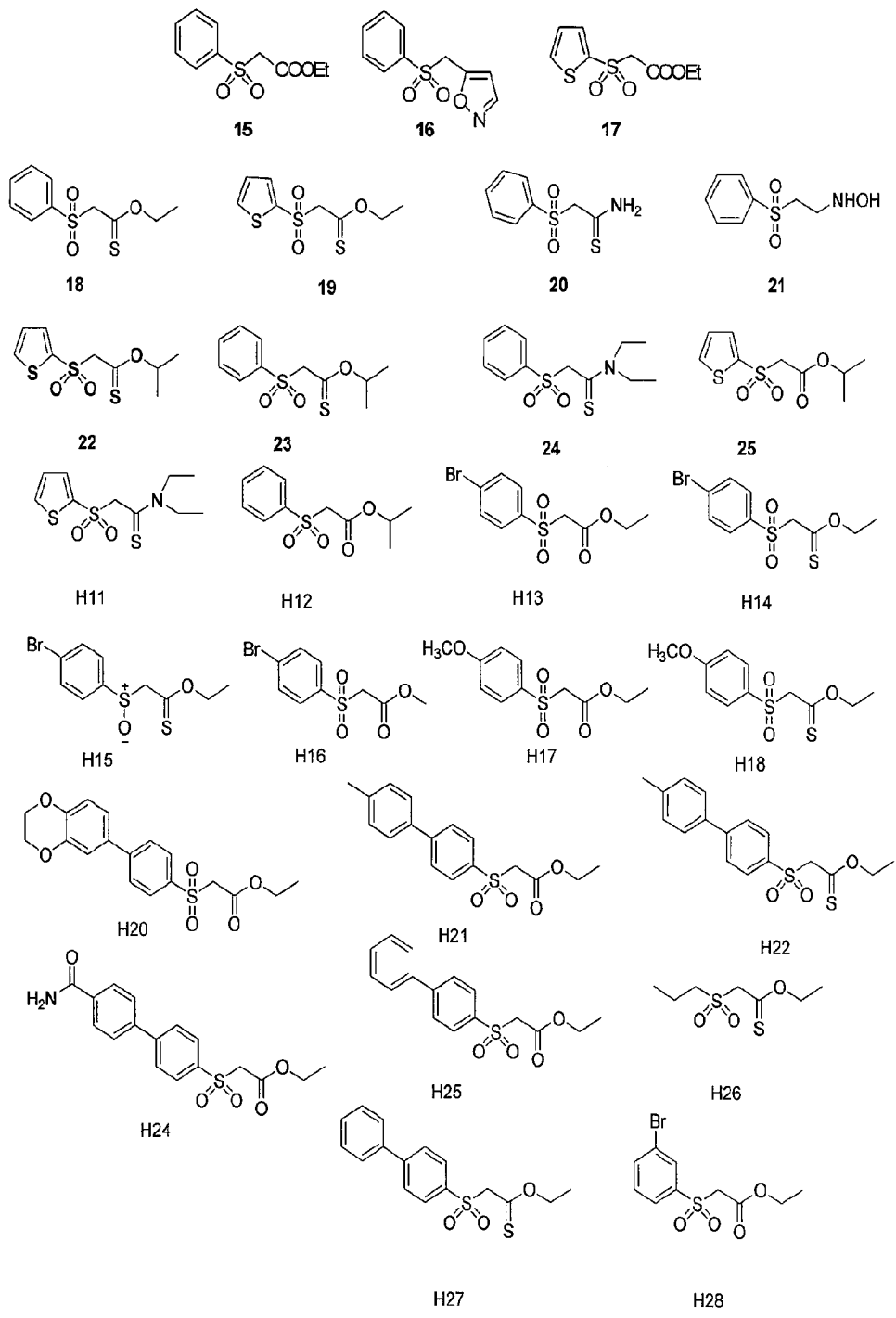
FIG. 8 illustrates analogues of compounds 10 and 11.
Figure 9A:
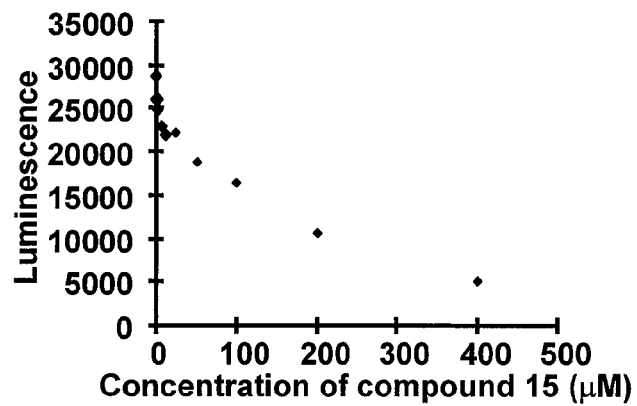
FIGS. 9A-9C illustrate graphs showing inhibitory curves for compound 15 (FIG. 9A) having an $IC_{50}$ of 170±30 μM; compound 16 (FIG. 9B) having an $IC_{50}$ of 150±30 μM; compound 17 (FIG. 9C) having an $IC_{50}$ of 124±16 μM. Concentrations of the compounds are, from high to low, 400 μM, 200 μM, 100 μM, 50 μM, 25 μM, 12.5 μM, 6.4 μM, 3.2 μM, 1.6 μM, 0.8 μM, and 0 μM.
Figure 9B:
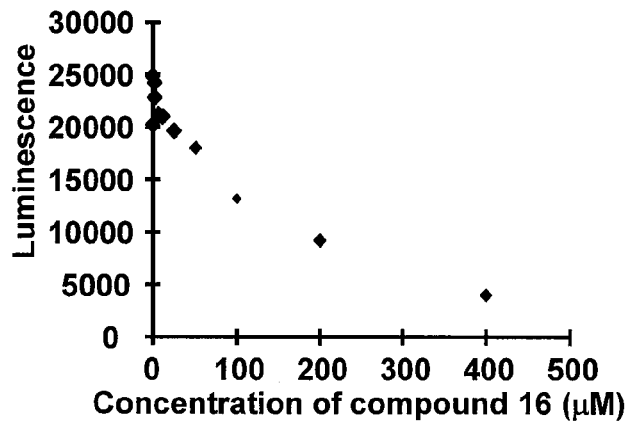
Figure 9C:
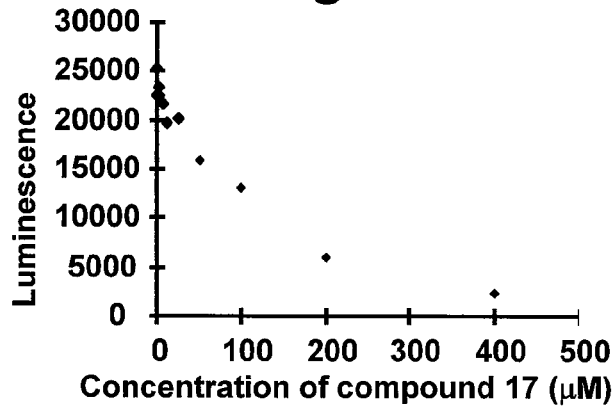

For these two active compounds, their ability to inhibit bacterial growth was examined. Results showed that they have no effect on bacterial growth (see FIGS. 6A-6C) indicating that their effect on bioluminescence production was due to AI-2 inhibition and not growth inhibition. Of 42 compounds screened found, five (FIG. 7) were found to be effective.

TABLE 1

Virtual screening results for the activity compounds
(each was tested at least 3 times)

| Compound No. | 10 | 11 | 12 | 13 | 14 |
|---|---|---|---|---|---|
| IC$_{50}$ value (μM) | 34.5 ± 2.5 | 55.0 ± 7.0 | 110 ± 31 | 87.8 ± 7.0 | 60.1 ± 39.9 |

TABLE 2

Analogs of virtual screening results for the activity
compounds (each was tested at least 3 times)

| Compound No. | 15 | 16 | 17 | 18 |
|---|---|---|---|---|
| IC$_{50}$ value (μM) | 170 ± 30 | 150 ± 30 | 124 ± 16 | 33 ± 4 |
| Compound No. | 19 | 20 | 21 | 22 |
| IC$_{50}$ value (μM) | 22 ± 2 | 89 ± 10 | 267 ± 49 | 34 ± 2 |
| Compound No. | 23 | 24 | 25 | |
| IC$_{50}$ value (μM) | 33 ± 4 | 91 ± 14 | 127 ± 21 | |
| Compound No. | H11 | H12 | H13 | H14 |
| IC$_{50}$ value (μM) | 138 ± 25 | 38.3 ± 15.1 | 16.8 ± 2.5 | 13.8 ± 2.0 |
| Compound No. | H15 | H16 | H17 | H18 |
| IC$_{50}$ value (μM) | 47.7 ± 14.2 | 80.9 ± 2.4 | 87.3 ± 5.6 | 26.0 ± 3.5 |
| Compound No. | H20 | H21 | H22 | H24 |
| IC$_{50}$ value (μM) | 157 ± 43 | 8.2 ± 2.3 | 5.6 ± 1.3 | 31.3 ± 23 |
| Compound No. | H25 | H26 | H27 | H28 |
| IC$_{50}$ value (μM) | 8.7 ± 2.9 | 21.6 ± 2.9 | 5.7 ± 0.8 | 162 ± 22 |

Example 3

Boronic Acids can Competitively Antagonize AI-2-Induced Quorum Sensing.

In addition to the compounds identified from virtual screening, several boronic acids were also studied for their inhibition of luminescence production in *V. harveyi*. Since both boronic acid and boric acid can bind to diol-containing compounds, boronic acids might be expected to sequester DPD and trap it in various inactive forms (shown as 5b, 6b, 8b, 9b, and 7b-d in Scheme 1, FIG. 1) and, therefore, lower the effective concentration of DPD. This, in turn, would result in the lowering of luminescence intensity. It should be noted that there was only one biologically active form of the boric acid-DPD complex (5a). However, a boronic acid can trap DPD in 7 biologically inactive forms (5b, 6b, 8b, 9b, and 7b-d of Scheme 1, FIG. 1). Boronic acid might also act as a mimic of the DPD-boric acid complex because both could exist in the anionic tetrahedral form when complexed with a diol.

Figure 10A:
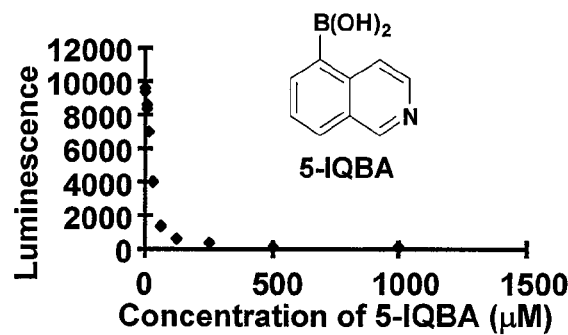
FIGS. 10A-10C illustrate graphs showing inhibitory curves for 5-IQBA (26) (FIG. 10A) having an $IC_{50}$ of 30.4±7.9 μM); 4-IQBA (27) (FIG. 10B) having an $IC_{50}$ of 66.1±8.9 μM; DDCQ (28) (FIG. 10C) having an $IC_{50}$ of 121.1±34.9 μM. Concentrations of boronic acids are from high to low 1 mM, 0.5 mM, 0.25 mM, 0.125 mM, 64 μM, 32 μM, 16 μM, 8 μM, 4 μM, 2 μM, and 0 μM.
Figure 10B:
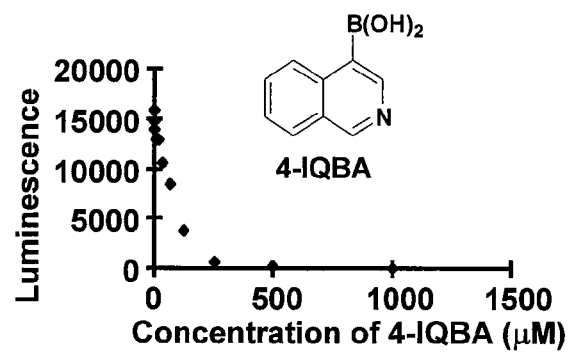
Figure 10C:
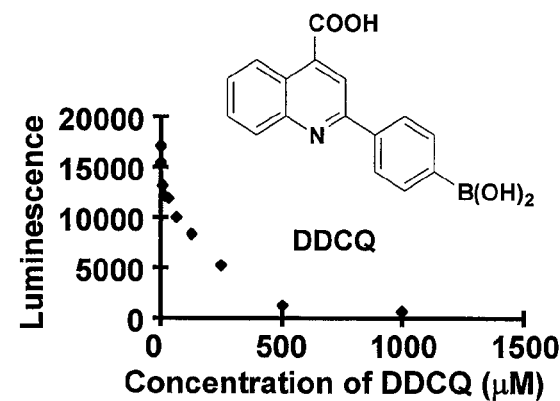
Figure 11A:
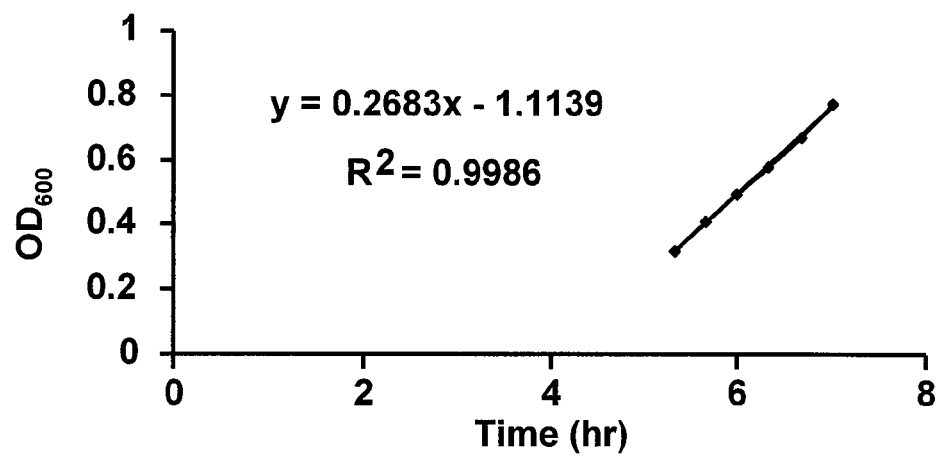
FIGS. 11A-11D are graphs illustrating bacterial growth curves.
Figure 11B:
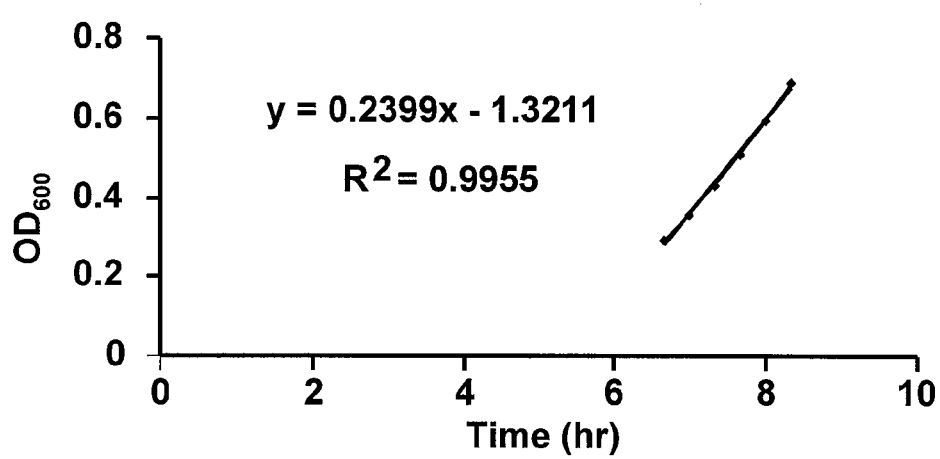
Figure 11C:
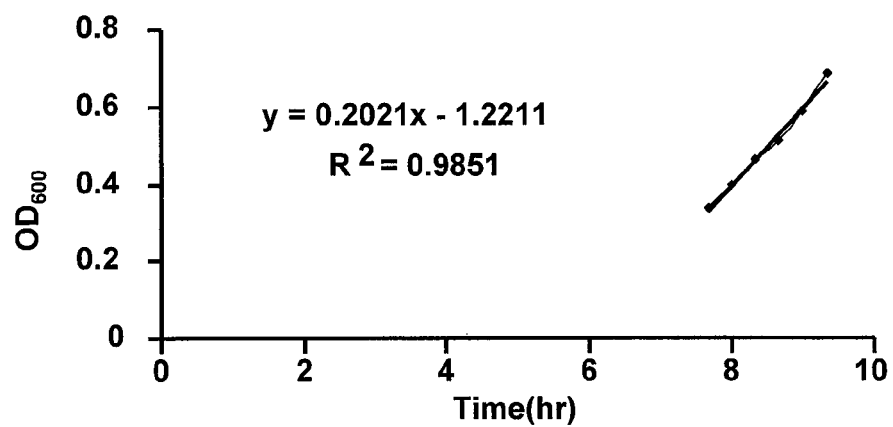
Figure 11D:
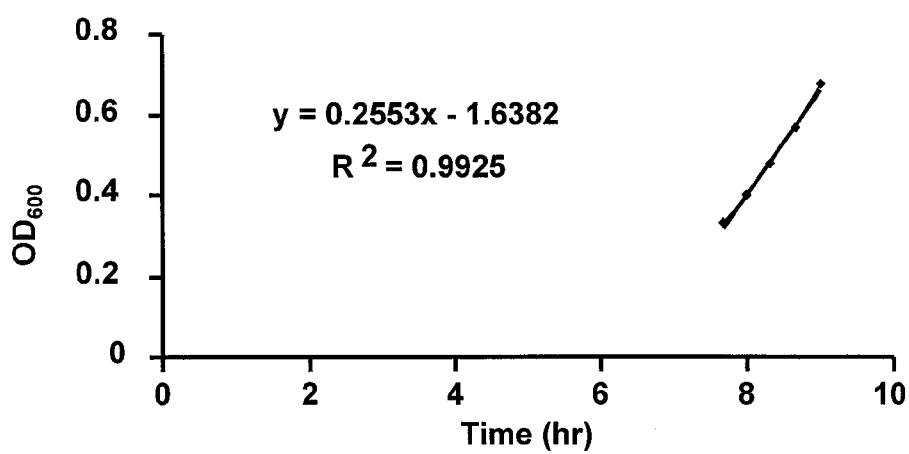
Figure 12A:
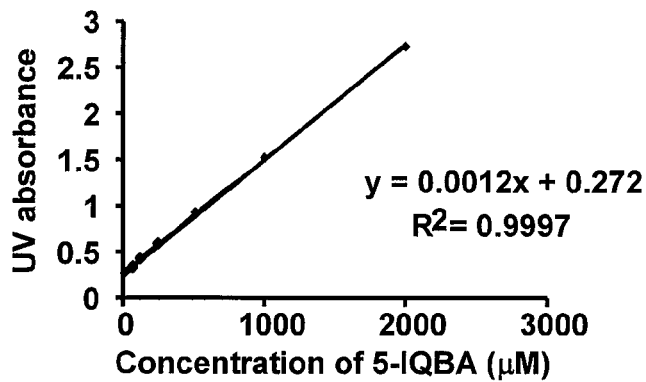
FIGS. 12A-12C illustrate graphs showing a solubility curve for 5-IQBA (FIG. 12A), 4-IQBA (FIG. 12B), and DDCQ (FIG. 12C). Concentrations of compounds are, from high to low, with 2-fold serial dilutions starting with 2000 μM for compound 5-IQBA, 500 μM for 4-IQBA and 250 μM for DDCQ.
Figure 12B:
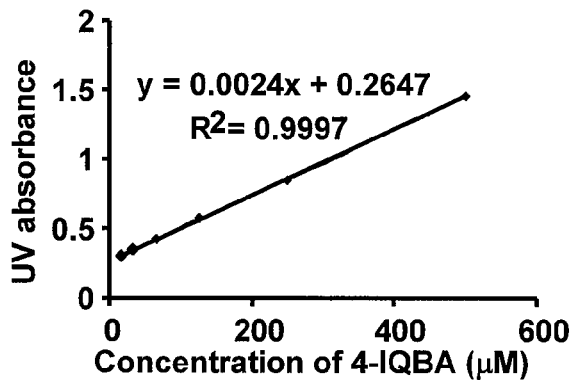
Figure 12C:
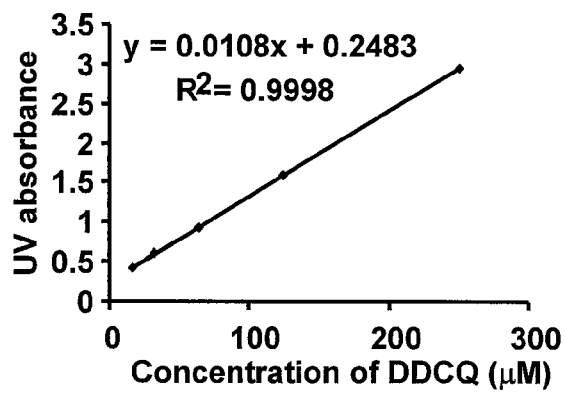

For this study, three boronic acids were selected as shown in FIG. 10. FIG. 10 also shows the effect of various boronic acids on the luminescence intensity of *V. harveyi*. All three compounds, 5-IQBA, 4-IQBA, and DDCQ, showed inhibition of DPD-induced luminescence emission by *V. harveyi*, with IC$_{50}$ values of 30, 66, and 121 μM for compounds 5-IQBA (26), 4-IQBA (27), and DDCQ (28), respectively. To make sure that the observed luminescence intensity changes were not due to inhibition of bacterial growth, the effect of these boronic acids on bacterial growth was also studied. The results as shown in FIGS. 11A-11D, indicated that no significant inhibition could be attributed to the inhibition of bacterial growth. The solubilities of the compounds at the test concentrations were also determined as shown in FIGS. 12A-12C. The linear relationship of these boronic acids, when dissolved in the AB medium, between concentration-UV absorption indicated that there is no solubility problem.

Example 4

Other boronic acids, the structures of which are shown in FIGS. 13 and 14 also showed activities, as shown in Table 3 (below). The low IC$_{50}$ values for some compounds suggest that their mechanism of action is possibly through direct binding to LuxP since the general affinity of boronic acids for DPD would not be expected to surpass a K$_d$ of less than high micromolar values.

TABLE 3

IC$_{50}$ values of selected boronic acids tested for their inhibition of
AI-2-mediated quorum sensing (each one was tested 3 times or more)

| Compound No. | 29 | 30 | 31 | 32 | 33 | 34 |
|---|---|---|---|---|---|---|
| IC$_{50}$ value (μM) | 11.8 ± 0.9 | 19.5 ± 15.5 | 26.9 ± 5.1 | 16.7 ± 2.2 | 9.1 ± 6.9 | 4.8 ± 2.0 |
| Compound No. | 35 | 36 | 37 | 38 | 39 | 40 |
| IC$_{50}$ value (μM) | 4.1 ± 1.3 | 3.7 ± 1.2 | 10.3 ± 1.2 | 16.6 ± 0.1 | 120.7 ± 4.3 | 3.6 ± 0.4 |
| Compound No. | 41 | 42 | 43 | 44 | 45 | 46 |
| IC$_{50}$ value (μM) | 369.2 ± 17.8 | 123.7 ± 31.7 | 13.1 ± 0.6 | 52.5 ± 19.8 | 22.3 ± 2.2 | 5.7 ± 3.5 |
| Compound No. | 47 | 48 | 49 | 50 | 51 | 52 |
| IC$_{50}$ value (μM) | 221.1 ± 54.3 | 17.0 ± 8.0 | 11.5 ± 3.5 | 19.8 ± 0.7 | 81.2 ± 51.1 | 39.3 ± 12.0 |

All compounds were tested at least three times

FIG. 14 illustrates the structures of boronic acids that have inhibitory effects as well as cytotoxicity. Table 4 below shows $IC_{50}$ values of boronic acids in their inhibition of AI-2-mediated quorum sensing.

TABLE 4

Compound number and their $IC_{50}$ value.
(each one was tested 3 times or more)

| Compound No. | 53 | 54 | 55 | 56 |
|---|---|---|---|---|
| $IC_{50}$ (μM) | 3.2 ± 1.7 | 1.3 ± 0.3 | 2.2 ± 1.9 | 8.6 ± 2.8 |
| Compound No. | 57 | 58 | 59 | 60 |
| $IC_{50}$ (μM) | 7.0 ± 2.0 | 6.8 ± 3.7 | 2.4 ± 1.4 | 5.1 ± 3.2 |

Example 5

Figure 15A:
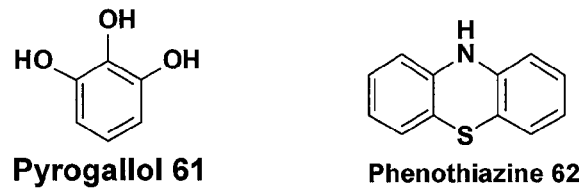
FIGS. 15A-15C illustrate graphs showing compounds (61) and (62) (FIG. 15A) and inhibitory curves for compound (61) (FIG. 15B) and an $IC_{50}$ of 2.0±1.2 μM, and for compound (62) (FIG. 15C) and an $IC_{50}$ of 10.7±3.7 μM). Concentrations of compound (61) are from high to low 20 μM, 10 μM, 5 μM, 2.5 μM, 1.25 μM, 0.64 μM, 0.32 μM, 0.16 μM, 0.08 μM, 0.04 μM, 0 μM. Concentrations of compound (62) are from high to low 100 μM, 50 μM, 25 μM, 12.5 μM, 6.4 μM, 3.2 μM, 1.6 μM, 0.8 μM, 0.4 μM, 0.2 μM, 0 μM.
Figure 15B:
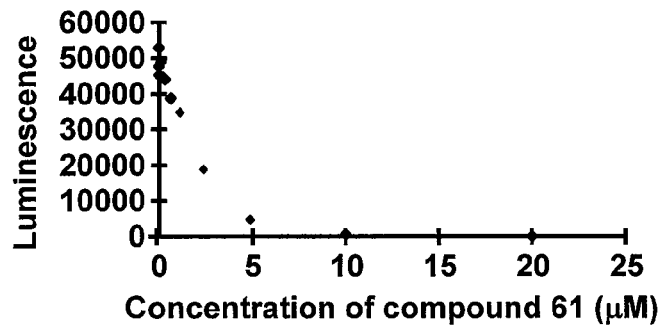
Figure 15C:
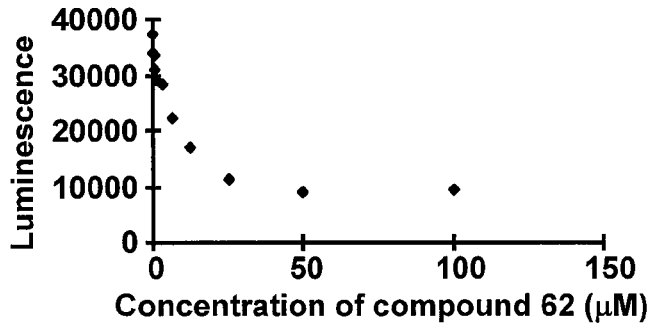
Figure 16:
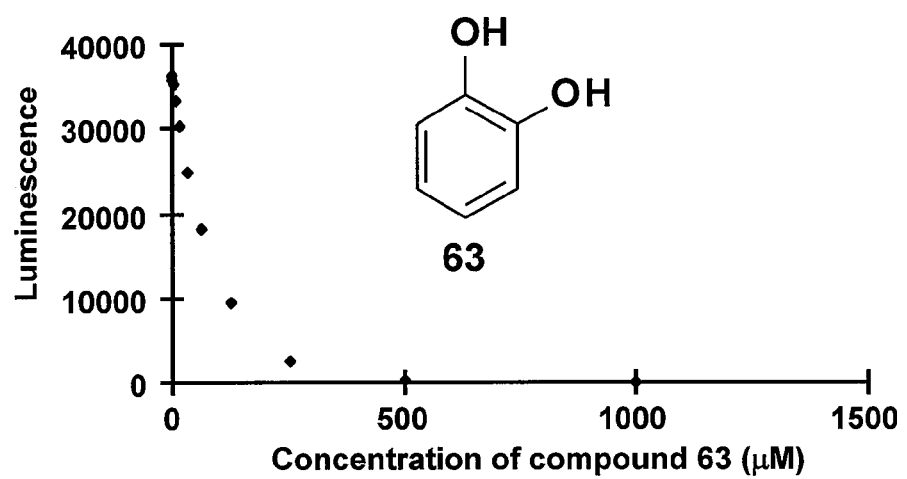
FIG. 16 illustrates the inhibitory curve of compound (63) and an $IC_{50}$ of 59±9 μM. Concentrations of compound (63) are from high to low 1 mM, 0.5 mM, 0.25 mM, 0.125 mM, 64 μM, 32 μM, 16 μM, 8 μM, 4 μM, 2 μM, and 0 μM.
Figure 17A:
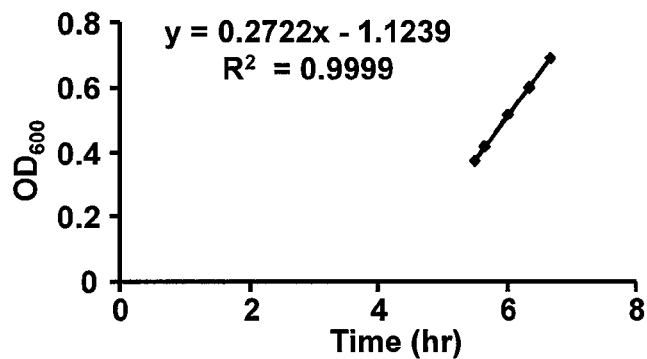
FIGS. 17A-17C illustrate graphs showing the growth curves for a control (FIG. 17A) having a doubling time of 78.9 min; compound (61) (FIG. 17B) at 5 μM having a doubling time of 78.4 min); compound (62) (FIG. 17C) at 20 μM having a doubling time of 72.3 min.
Figure 17B:
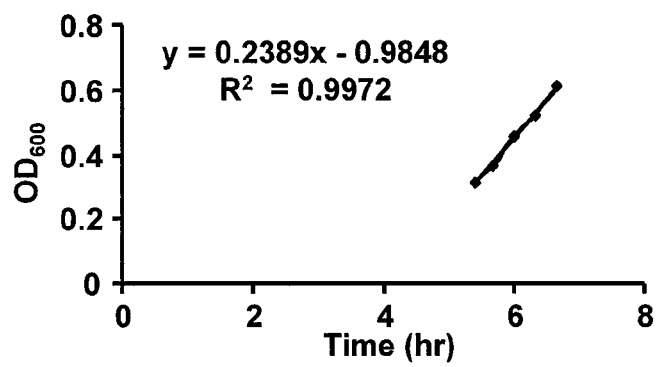
Figure 17C:
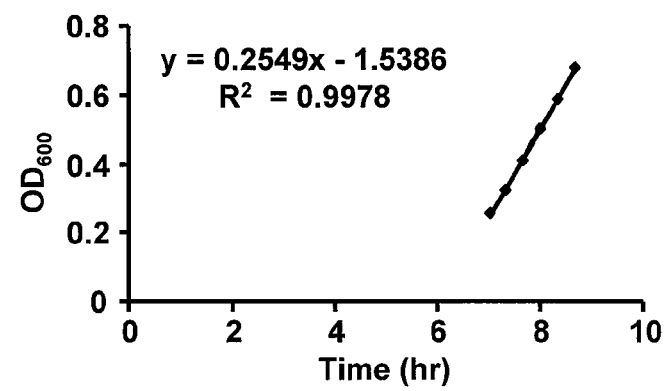

Two compounds showed especially potent activities: pyrogallol (61, $IC_{50}$, 2 μM) and phenothiazine (62, $IC_{50}$, 10 μM) shown in FIG. 15A. The pyrogallol's activity may have been through its complexation with boric acids, which mimics the DPD-boric acid complex. The third hydroxyl group might also interact with LuxP through interactions such as H-bond since the activity of catechol (63) is lower than pyrogallol as shown in FIG. 17. Phenothiazine most likely exerted its effect through direct binding to LuxP.

Example 6

Bacterial growth inhibition tests indicated that the inhibitory effect of 61 and 62 on bioluminescence was not due to growth inhibition as shown in FIGS. 18 and 19.

Analogs of 61 and 62 were also tested. FIG. 18 illustrates structures of phenothiazine and its analogues that had inhibitory effects. Table 5 below shows the $IC_{50}$ values in the inhibition of AI-2-mediated quorum sensing (each was tested three times or more).

TABLE 5

$IC_{50}$ values of phenothiazine and analogues
(each one was tested 3 times or more)

| Compound No. | 62 | 64 | 65 | 66 |
|---|---|---|---|---|
| $IC_{50}$ (μM) | 10.7 ± 3.7 | 106.8 ± 26.6 | 91.3 ± 33.7 | 92.1 ± 17.1 |
| Compound No. | 67 | 68 | 69 | 70 |
| $IC_{50}$ (μM) | 105.8 ± 19.2 | 179.9 ± 29.9 | 47.1 ± 4.6 | 61.3 ± 15.6 |

FIG. 19 illustrates the structures of pyrogallol and its analogues that have inhibitory effects. Table 6 below shows $IC_{50}$ values in the inhibition of AI-2-mediated quorum sensing (each one was tested three times or more).

TABLE 6

$IC_{50}$ values of pyrogallol and analogues
(each one was tested 3 times or more)

| Compound No. | 61 | 63 | 71 | 72 |
|---|---|---|---|---|
| $IC_{50}$ value (μM) | 2.0 ± 1.2 | 59.0 ± 9.0 | 21.3 ± 2.6 | 12.3 ± 6.3 |

TABLE 6-continued $IC_{50}$ values of pyrogallol and analogues
(each one was tested 3 times or more)

| Compound No. | 73 | 74 | 75 | 76 |
|---|---|---|---|---|
| $IC_{50}$ value (μM) | 3.7 ± 1.2 | 2.9 ± 0.9 | 61.4 ± 9.6 | 11.8 ± 1.4 |
| Compound No. | 77 | 78 | 79 | 80 |
| $IC_{50}$ value (μM) | 21.8 ± 0.8 | 4.0 ± 2.3 | 49.9 ± 9.1 | 3.2 ± 1.0 |

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified. In addition, the phrase "about 'x' to 'y'" includes "about 'x' to about 'y'".

It should be emphasized that the above-described embodiments of the present disclosure are merely possible examples of implementations, and are merely set forth for a clear understanding of the principles of this disclosure. Many variations and modifications may be made to the above-described embodiment(s) of the disclosure without departing substantially from the spirit and principles of the disclosure. All such modifications and variations are intended to be included herein within the scope of this disclosure and protected by the following claims.

What is claimed:

1. A compound selected from the group consisting of the formulas:

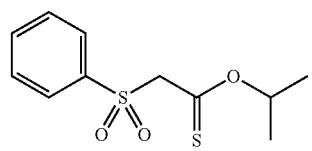

23

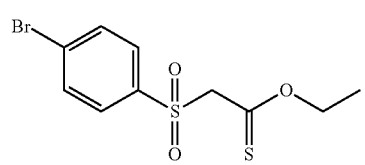

H14

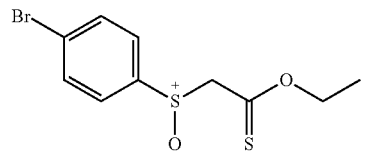

H15

-continued
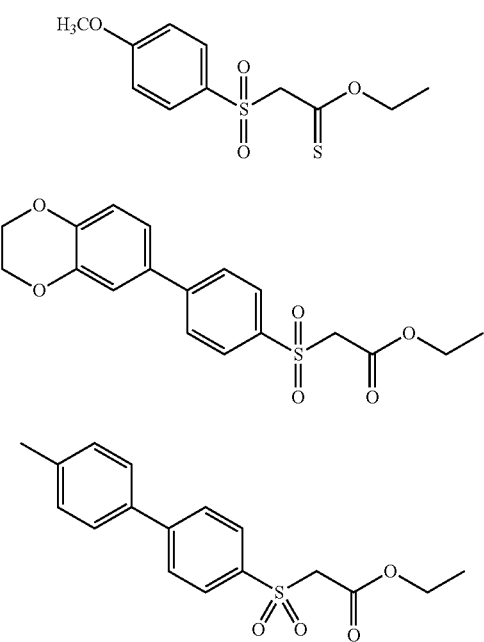
H18
H20
H21
H22
H24
H27
H28
2. A composition consisting of at least one compound selected from the group consisting of the formulas:
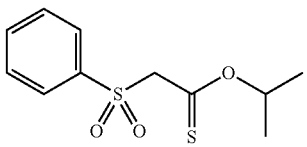
23
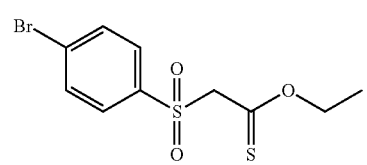
H14
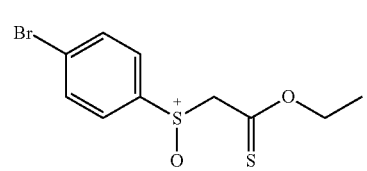
H15
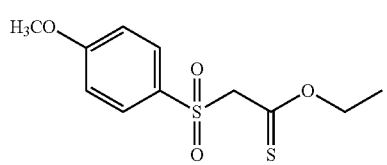
H18
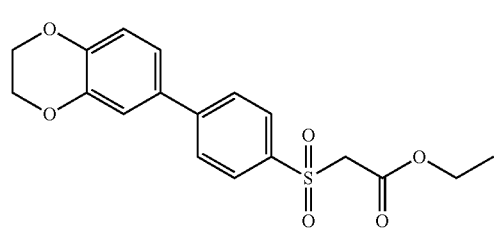
H20
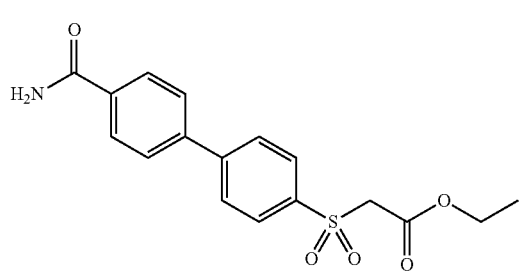
H21
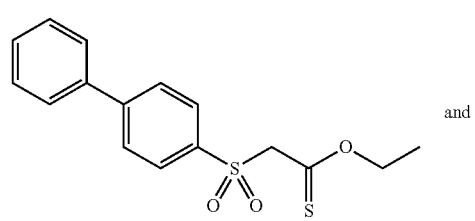
H22
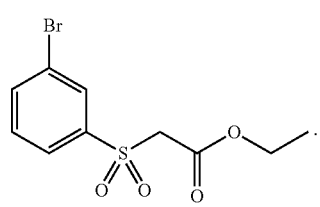

-continued

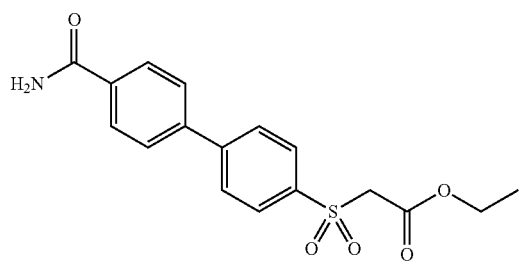
H24

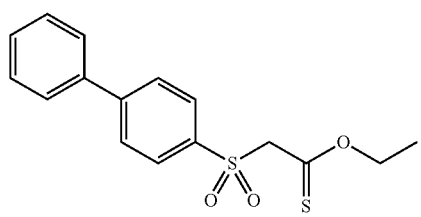
H27

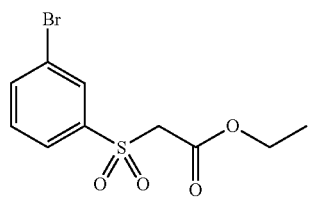
H28 and a carrier, wherein the compound in said composition is in an amount effective for modulating quorum sensing of a microbial population.

3. The composition of claim 2, wherein the carrier is a pharmaceutically acceptable carrier.

4. A compound selected from the group consisting of the formulas:

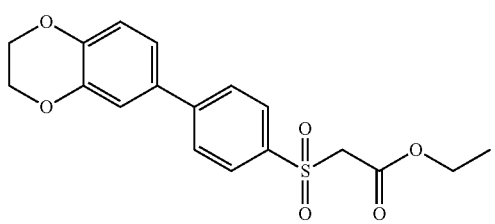
H20

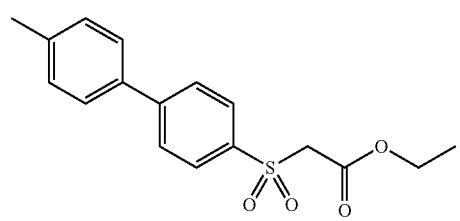
H21

-continued

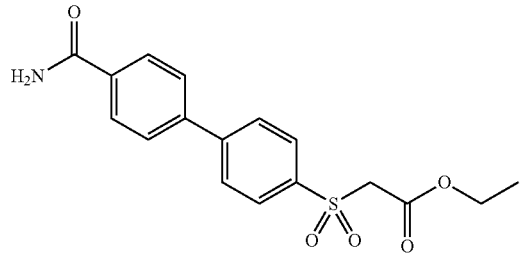
H24

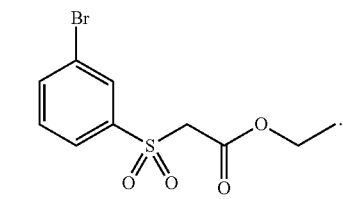
H28

5. A compound selected from the group consisting of the formulas:

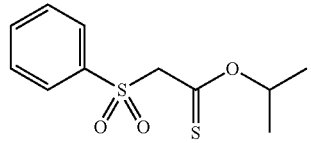
23

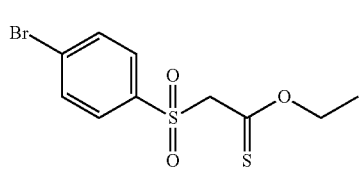
H14

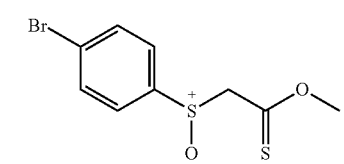
H15

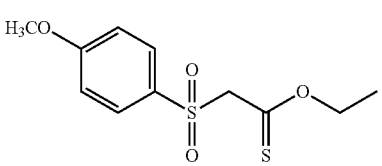
H18

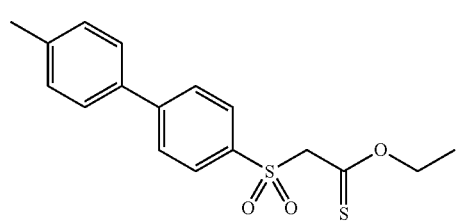
H22

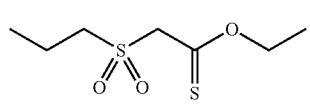
H26

-continued
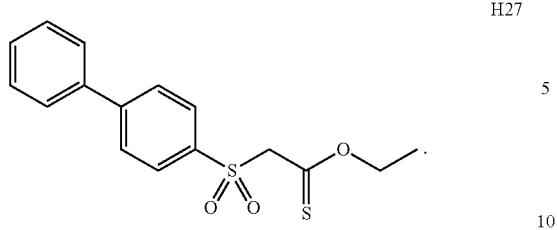
6. A compound, wherein said compound has the formula:
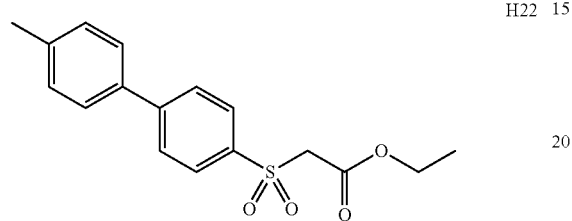
* * * * *

UNITED STATES PATENT AND TRADEMARK OFFICE
CERTIFICATE OF CORRECTION

PATENT NO. : 8,653,258 B2  Page 1 of 1
APPLICATION NO. : 12/597825
DATED : February 18, 2014
INVENTOR(S) : Wang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 399 days.

Signed and Sealed this

Twenty-ninth Day of September, 2015

Michelle K. Lee
*Director of the United States Patent and Trademark Office*